(12) United States Patent
Nie et al.

(10) Patent No.: US 12,264,186 B2
(45) Date of Patent: Apr. 1, 2025

(54) HUMAN HEPATOCYTE GROWTH FACTOR MUTANT AND USES THEREOF

(71) Applicant: BEIJING NORTHLAND BIOTECH CO., LTD., Beijing (CN)

(72) Inventors: Liya Nie, Beijing (CN); Songshan Xu, Beijing (CN); Suyong Ma, Beijing (CN)

(73) Assignee: BEIJING NORTHLAND BIOTECH CO., LTD., Beijing (CN)

( * ) Notice: Subject to any disclaimer, the term of this patent is extended or adjusted under 35 U.S.C. 154(b) by 656 days.

(21) Appl. No.: 17/420,865

(22) PCT Filed: Jan. 2, 2020

(86) PCT No.: PCT/CN2020/070010
§ 371 (c)(1),
(2) Date: Jul. 6, 2021

(87) PCT Pub. No.: WO2020/143515
PCT Pub. Date: Jul. 16, 2020

(65) Prior Publication Data
US 2022/0064242 A1   Mar. 3, 2022

(30) Foreign Application Priority Data

Jan. 7, 2019   (CN) .................. 201910010091.X

(51) Int. Cl.
| | | |
|---|---|---|
| C07K 14/475 | (2006.01) | |
| A61K 38/00 | (2006.01) | |
| A61P 3/10 | (2006.01) | |
| A61P 9/10 | (2006.01) | |
| A61P 25/02 | (2006.01) | |

(52) U.S. Cl.
CPC ............ *C07K 14/4753* (2013.01); *A61P 3/10* (2018.01); *A61P 9/10* (2018.01); *A61P 25/02* (2018.01); *A61K 38/00* (2013.01)

(58) Field of Classification Search
CPC ........ C07K 14/4753; A61P 9/10; A61P 25/02; A61P 3/10; A61K 38/00
See application file for complete search history.

(56) References Cited

U.S. PATENT DOCUMENTS

| 10,213,485 | B2 | 2/2019 | Fukuta et al. | |
|---|---|---|---|---|
| 2007/0010443 | A1* | 1/2007 | Detmar | A61P 17/06 514/19.3 |
| 2012/0010273 | A1 | 1/2012 | Kim et al. | |
| 2017/0333527 | A1 | 11/2017 | Fukuta et al. | |

FOREIGN PATENT DOCUMENTS

| CA | 2675953 A1 | 9/2008 |
|---|---|---|
| CN | 1284563 A | 2/2001 |
| CN | 1643149 A | 7/2005 |
| CN | 106714823 A | 5/2017 |
| CN | 108424459 A | 8/2018 |
| CN | 109535243 A | 3/2019 |
| EP | 1036566 A1 | 9/2000 |
| WO | 93/23541 A1 | 11/1993 |
| WO | 98/51798 A1 | 11/1998 |
| WO | 99/27951 A1 | 9/2002 |
| WO | 02/088354 A1 | 11/2002 |
| WO | 2008/105507 A1 | 6/2010 |
| WO | 2016/039163 A1 | 6/2017 |

OTHER PUBLICATIONS

Water, from http://www.biology-online.org/dictionary/Water, accessed Apr. 24, 2014, pp. 1-3.*
Database Accession No. AAB52574, *Xenopus laevis* (African clawed frog) growth factor Livertine, Database EMBL [Online], 2 pages (Jul. 2, 1996).
Database Accession No. CAA58862, "*Gallus gallus* (chicken) hepatocyte growth factor-like/macrophage stimulating protein," Database EMBL [Online], 2 pages, (Dec. 19, 1995).
Supplementary European Search Report for EP Application No. 20 73 8308, 11 pages, dated Apr. 7, 2022.
Funakoshi et al., "ALS and Neurotrophic Factors—HGF as a Novel Neurotrophic and Neuroregenerative Factor," *Brain and Nerve* 59(10):1195-1202, 2007.
Ruiz et al., "Involvement of Livertine, a hepatocyte growth factor family member, in neural morphogenesis," *Mechanisms of Development* 60:207-220, 1996.
NCBI Reference Sequence: NP_000592.3, hepatocyte growth factor isoform 1 preproprotein [*Homo sapiens*], 4 pages (May 16, 2021).
Tolbert et al., "Structural basis for agonism and antagonism of hepatocyte growth factor," *PNAS* 107(30):13264-13269 (2010).
Xu et al., "Production of Human Mutant Biologically Active Hepatocyte Growth Factor in Chinese Hamster Ovary Cells," Accepted Manuscript, Laboratory of Molecular Pharmacology, School of Pharmaceutical Sciences, Jiangnan University, Wuxi, China, Jiangsu Institute of Hematology, the First Affiliated Hospital of Soochow University, Suzhou, China, Cyrus Tang Hematology Center and Ministry of Education Engineering Center of Hematological Disease, Soochow University, Suzhou, China, 24 pages (2016).

\* cited by examiner

*Primary Examiner* — Li N Komatsu
(74) *Attorney, Agent, or Firm* — Seed IP Law Group LLP

(57) ABSTRACT

Disclosed is a human hepatocyte growth factor (hHGF) mutant. Also disclosed are a nucleic acid molecule encoding the mutant, a carrier containing the nucleic acid molecule, and a host cell containing the nucleic acid molecule or the carrier. At the same time disclosed are a pharmaceutical composition comprising the hHGF mutant or the nucleic acid molecule encoding the mutant, and the uses of the hHGF mutant or the nucleic acid molecule encoding the mutant.

10 Claims, 1 Drawing Sheet
Specification includes a Sequence Listing.

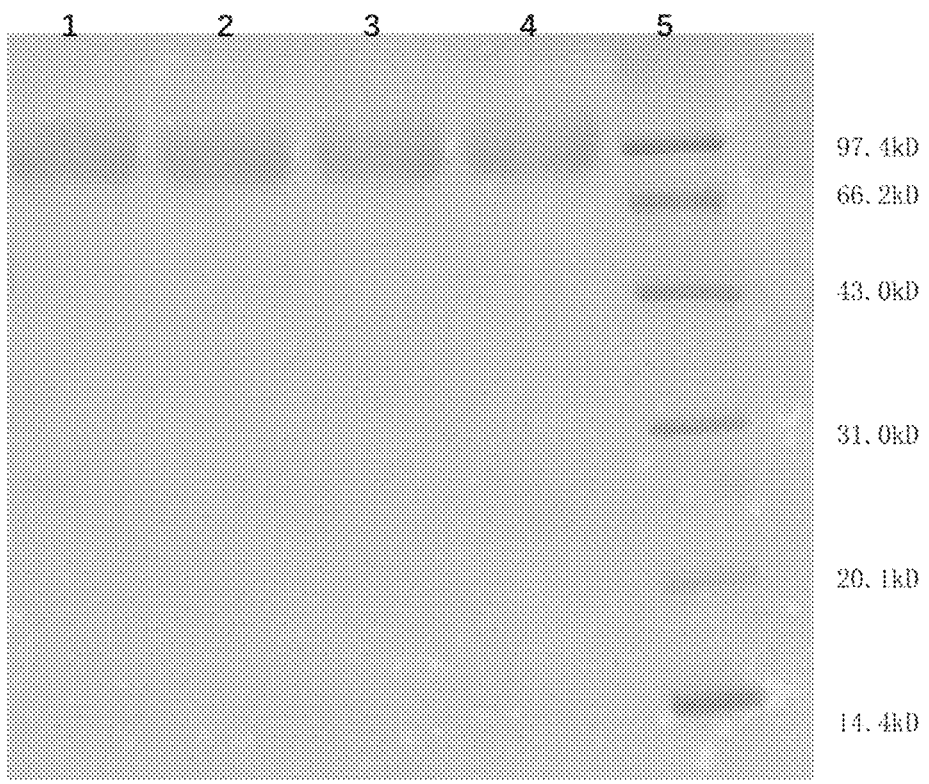

HUMAN HEPATOCYTE GROWTH FACTOR MUTANT AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 140162_402USPC_SEQUENCE_LISTING.txt. The text file is 38.8 KB, was created on Jul. 2, 2021, and is being submitted electronically via EFS-Web.

TECHNICAL FIELD

The present application relates to a mutant of human hepatocyte growth factor (hHGF). The present application also relates to a nucleic acid molecule encoding the mutant, a vector comprising the nucleic acid molecule, and a host cell comprising the nucleic acid molecule or vector. The present application also relates to a pharmaceutical composition comprising the hHGF mutant or the nucleic acid molecule encoding the mutant, as well as a use of the hHGF mutant or the nucleic acid molecule encoding the mutant. The hHGF mutant or the nucleic acid molecule encoding the mutant can be used, for example, for promotion of endothelial cell growth and/or migration, promotion of the formation of a blood vessel, or treatment of a disease that can benefit from the activity of a natural hHGF (e.g., treatment of lower extremity artery ischemia, myocardial infarction and/or diabetic peripheral neuropathy), and therefore can be used for manufacture of a medicament.

BACKGROUND

Hepatocyte growth factor (HGF) is initially isolated from rat plasma and platelets, and is a secreted heparin affinity glycoprotein, also known as scatter factor (SF). It is now known that HGF is produced by mesenchymal cells, binds to the receptor c-Met and activates the receptor's tyrosine kinase activity, and promotes the growth, migration and morphogenesis of liver cells, epithelial cells, endothelial cells, melanocytes, hematopoietic cells and other types of cells. HGF plays an important role in the development of embryonic liver and placenta, participates in maintaining and renewing the cells of liver, lung, kidney and other organs, and promotes the regeneration of these organs and repair of these organs after injury. In addition, HGF has pro-invasion or growth-inhibiting effects on tumor cells from different sources. Therefore, HGF is a multifunctional cytokine with broad clinical application prospects.

Mature HGF is a heterodimer composed of heavy chain (α chain) and light chain (β chain) connected by interchain disulfide bonds, in which the α chain contains 463 amino acids, about 69 kD; the β chain contains 234 amino acids, about 34 kD. The N-terminus of the α chain has a hairpin structure, and near its C-terminus there are 4 plasmin-like Kringle structures (called K1, K2, K3, K4 regions in turn), each Kringle structure is composed of about 80 amino acids. It is now known that the hairpin structure and K1 region are the key parts for HGF to bind to the receptor c-Met; and the hairpin structure and K2 region together constitute the necessary structure for the affinity of HGF with heparin and heparan sulfate; the β chain contains serine protease-like folding region, but has no serine protease activity. The entire HGF molecule has 4 N-glycosylation sites, located at Asn 294, Asn 402, Asn 566 and Asn 653, respectively, and the heavy chain and light chain each contain 2 N-glycosylation sites (Molecular biology research of hepatocyte growth factor. Journal of Bioengineering, 2002, 18:1-4).

C-Met is a specific cell membrane receptor of HGF, which is expressed in a variety of cells, such as cardiomyocytes, vascular endothelial cells, etc., and mediates the biological effects of HGF. The HGF/C-Met system is widely expressed in a variety of tissues and participates in the regulation of cell growth, movement and tissue morphogenesis and other complex biological processes. HGF is an endothelial growth factor, which binds to its specific receptor C-Met, causes phosphorylation of receptor tyrosine residues, and initiates the post-receptor signal transduction process; it also causes phosphorylation of ERK, leading to STAT3 (Ser727) phosphorylation to form a dimer and enter into the nucleus, promoting the expression of early growth response genes such as c-fos, thereby regulating cell growth at the transcriptional level. The study also found that HGF can activate MEK, P42/44MAPK and P90RSR, reduce cell death caused by hydrogen peroxide, and can activate BCL-2 gene expression and inhibit the translocation of Bax protein to the mitochondrial membrane surface, maintaining electrochemical gradient inside and outside the mitochondrial membrane, and preventing the leakage of cytochrome C in the mitochondria, inhibiting the activity of Caspase-3 and Caspase-9, thereby exerting anti-apoptotic effects. HGF can also stimulate the expression of MMP-1, VEGF, HGF and C-Met in vascular endothelial cells and vascular smooth muscle cells, and significantly increase the mRNA expression and transcriptional activity of Ets-1, playing an important role in the process of neovascularization (Angiogenic property of hepatocyte growth factor is dependent on upregulation of essential transcription factor for the formation of a blood vessel, ets-1. Circulation, 2003, 107:1411-1417). The Ets pathway is also one of the molecular mechanisms by which HGF promotes the formation of a blood vessel (Therapeutic the formation of a blood vessel using hepatocyte growth factor. Current Gene Therapy, 2004, 4: 199-206). The Ets family transcription factor has a DNA-binding domain, can bind to the core of the DNA sequence GGA, plays a very important role in the expression of a variety of genes involved in mitogenic signals, and may participate in the regulation of the formation of a blood vessel by controlling the transcription of these genes. HGF gene contains many regulatory regions, such as B cell and macrophage-specific transcription factor junction region, interleukin 26 response element (IL26RE), transforming growth factor inhibitory element (TNFIE) and cAMP response element (CRE). Therefore, exogenous HGF can stimulate the expression of endogenous HGF by inducing the activity of ets, and the endogenous HGF can promote the formation of small blood vessels through automatic conduction function.

The inventors of the present application discovered after research that hHGF can be mutated to obtain a hHGF mutant with enhanced biological activity.

Contents of the Present Invention

In the present application, unless otherwise specified, the scientific and technical terms used herein have the meanings commonly understood by those skilled in the art. In addition, the laboratory procedures of cell culture, molecular genetics, nucleic acid chemistry, and immunology used herein are all routine procedures widely used in the corresponding fields. At the same time, in order to better understand the present application, the definitions and explanations of related terms are provided below.

As used herein, the terms "natural hHGF" and "wild-type hHGF" refer to human hepatocyte growth factor (hHGF) that is biologically active and naturally occurs, and both have the same meaning and can be used interchangeably. The amino acid sequence of natural hHGF or wild-type hHGF can be easily obtained from various public databases (e.g., GenBank database). For example, the amino acid sequence of natural hHGF can be found in GenBank database accession number: NP_000592.3.

As used herein, when referring to the amino acid sequence of nature hHGF, it is described by using the sequence shown in SEQ ID NO:1. For example, the expression "the $130^{th}$ amino acid residue of natural hHGF" refers to the $130^{th}$ amino acid residue of the protein shown in SEQ ID NO:1. However, those skilled in the art understand that natural hHGF may have a plurality of versions, which have substantially the same primary structure (i.e., amino acid sequence) and high-level structure (i.e., spatial structure), and substantially the same biological function, but they can still have slight differences in amino acid sequence. Therefore, in the present application, natural hHGF is not limited to the protein shown in SEQ ID NO:1, but is intended to cover all known natural hHGF. Therefore, in the present application, the term "nature hHGF" shall include various naturally-occurring hHGF with biological function, including, for example, the hHGF shown in SEQ ID NO:1 and its naturally-occurring variants. Moreover, when describing the amino acid position of hHGF, it includes not only the specific amino acid position in SEQ ID NO:1, but also the amino acid position in its natural variant corresponding to the specific amino acid position. For example, the expression "the $130^{th}$ amino acid residue of natural hHGF" includes the $130^{th}$ amino acid residue of SEQ ID NO:1, and the corresponding amino acid position in its natural variant. According to the present application, the expression "corresponding amino acid position" refers to the amino acid position at the equivalent position in the sequences to be compared when the sequences are optimally aligned, that is, when the sequences are aligned to obtain the highest percent identity. Similarly, the expression "position corresponding to the $130^{th}$ position of SEQ ID NO:1" refers to the amino acid position in the sequence to be compared that is equivalent to the $130^{th}$ position of SEQ ID NO:1 when the sequence is optimally aligned with SEQ ID NO:1, that is, when the sequence is aligned with SEQ ID NO:1 to obtain the highest percent identity.

In certain preferred embodiments, the natural hHGF has the amino acid sequence shown in SEQ ID NO: 1. In certain preferred embodiments, the natural hHGF is a naturally-occurring human hepatocyte growth factor with biological function, and its amino acid sequence has an identity of at least 85%, at least 90%, at least 95%, at least 96%, at least 97%, at least 98%, or at least 99% as compared with SEQ ID NO:1. In certain preferred embodiments, the natural hHGF is a naturally-occurring human hepatocyte growth factor with biological function, and its amino acid sequence has a difference of one or more (e.g., 1 to 10 or 1 to 5 or 1 to 3) amino acids (e.g., conservative substitution of amino acids).

As used herein, the term "identity" is used to refer to a sequence matching degree between two polypeptides or between two nucleic acids. When a certain position in the two sequences to be compared is occupied by the same base or amino acid monomer subunit (e.g., a certain position in each of the two DNA molecules is occupied by adenine, or a certain position in each of the two polypeptides is occupied by lysine), then each molecule is identical at that position. The "percent identity" between two sequences is a function of the number of matching positions shared by the two sequences divided by the number of compared positions×100. For example, if 6 out of 10 positions in two sequences match, then the two sequences have an identity of 60%. For example, the DNA sequences CTGACT and CAGGTT have an identity of 50% (3 out of 6 positions match). Generally, the comparison is carried out when two sequences are aligned to produce maximum identity. Such alignment can be achieved by using, for example, the method of Needleman et al. (1970) J. Mol. Biol. 48:443-453 that can be conveniently performed by a computer program such as the Align program (DNAstar, Inc.). The percent identity between two amino acid sequences could also be determined by using the algorithm of E. Meyers and W. Miller (Comput. Appl Biosci., 4:11-17 (1988)) integrated into the ALIGN program (version 2.0), and using the PAM120 weight residue table, gap length penalty of 12 and gap penalty of 4. In addition, the percent identity between two amino acid sequences could also be determined by using the algorithm of Needleman and Wunsch (J Mol Biol. 48:444-453 (1970)) integrated into the GAP program of GCG software package (available on <www.gcg.com>), and using the Blossum 62 matrix or PAM250 matrix, gap weight of 16, 14, 12, 10, 8, 6 or 4 and length weight of 1, 2, 3, 4, 5 or 6.

As used herein, the term "conservative substitution" or "conservative replacement" refers to an amino acid substitution or replacement that does not adversely affect or change the essential characteristics of the protein/polypeptide comprising the amino acid sequence. For example, the conservative substitution can be introduced by standard techniques known in the art such as site-directed mutagenesis and PCR-mediated mutagenesis. The conservative amino acid substitution includes a substitution in which an amino acid residue is substituted with an amino acid residue with similar side chain, for example, a substitution with an amino acid residue that is physically or functionally similar to the corresponding amino acid residue (e.g., having similar size, shape, charge, chemical properties, including the ability to form covalent bonds or hydrogen bonds, etc.). Families of amino acid residues with similar side chains have been defined in the art. These families include amino acids with basic side chains (e.g., lysine, arginine and histidine), acidic side chains (e.g., aspartic acid, glutamic acid), uncharged polar side chains (e.g., glycine, asparagine, glutamine, serine, threonine, tyrosine, cysteine, tryptophan), non-polar side chains (e.g., alanine, valine, leucine, isoleucine, proline, phenylalanine, methionine), (3-branched side chains (e.g., threonine, valine, isoleucine), and aromatic side chains (e.g., tyrosine, phenylalanine, tryptophan, histidine). Therefore, it is preferred to substitute the corresponding amino acid residue with another amino acid residue from the same side chain family. The methods of identifying conservative amino acid substitutions are well known in the art (see, for example, Brummell et al., Biochem. 32:1180-1187 (1993); Kobayashi et al. Protein Eng. 12(10):879-884 (1999); and Burks et al. Proc. Natl Acad. Set USA 94:412-417 (1997), which are incorporated herein by reference).

As used herein, the terms "polypeptide" and "protein" have the same meaning and can be used interchangeably. And in the present invention, amino acids are usually represented by one-letter and three-letter abbreviations well known in the art. For example, alanine can be represented by A or Ala.

As used herein, the term "amino acid with a basic side chain" has the meaning commonly understood by those skilled in the art. An amino acid usually has the following structure:

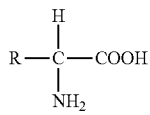

in which, R is a side chain group.

Therefore, when the side chain group R is basic, the amino acid is an amino acid with a basic side chain. In a solution of an amino acid with a basic side chain, the side chain of the amino acid can be dissociated to produce OH⁻, which is basic. Correspondingly, the side chain of the amino acid after dissociation will carry a positive charge. Therefore, an amino acid with a basic side chain is also referred to as a basic amino acid or an amino acid with a positively charged side chain group. Typical examples of an amino acid with a basic side chain include, but are not limited to, lysine, arginine, and histidine.

As used herein, the term "isolated" or "being isolated" refers to being obtained from a natural state by artificial means. If a certain substance or component in nature is "isolated", it may be that the natural environment in which it is located has changed, or the substance has been isolated from the natural environment, or both. For example, a certain unisolated polynucleotide or polypeptide naturally exists in a living animal, and the same polynucleotide or polypeptide with high purity isolated from this natural state is called as "isolated". The term "isolated" or "being isolated" does not exclude the mixing of artificial or synthetic materials, nor does it exclude the presence of other impure materials that do not affect the activity of the material.

As used herein, the term "vector" refers to a nucleic acid delivery vehicle into which a polynucleotide can be inserted. When the vector can express the protein encoded by the inserted polynucleotide, the vector is called an expression vector. The vector can be introduced into a host cell through transformation, transduction or transfection, so that the genetic material elements it carries can be expressed in the host cell. The vector is well-known to those skilled in the art, including but not limited to: plasmids (e.g., naked plasmids); phagemids; cosmids; artificial chromosomes such as yeast artificial chromosomes (YAC), bacterial artificial chromosomes (BAC) or P1-derived artificial chromosomes (PAC); bacteriophages such as λ bacteriophage or M13 bacteriophage; and, viral vectors, etc. Viruses that can be used as vectors include, but are not limited to, retrovirus (including lentivirus), adenovirus, adeno-associated virus, herpes virus (e.g., herpes simplex virus), poxvirus, baculovirus, papillomavirus, papovavirus (e.g., SV40). A vector can contain a variety of elements that control expression, including but not limited to, promoter sequences, transcription initiation sequences, enhancer sequences, selection elements, and reporter genes. In addition, the vector may also contain a replication origin site.

As used herein, the term "host cell" refers to a cell that can be used for the introduction of a vector, which includes, but is not limited to, prokaryotic cells such as *Escherichia coli* or *Bacillus subtilis*, fungal cells such as yeast cells or *Aspergillus*, etc., insect cells such as S2 *Drosophila* cells or Sf9, or animal cells such as fibroblasts, CHO cells, COS cells, NSO cells, HeLa cells, BHK cells, HEK 293 cells or human cells.

As used herein, the term "pharmaceutically acceptable" refers to being acceptable to animals, especially to humans, which is recognized in the pharmaceutical field. As used herein, the term "pharmaceutically acceptable carrier and/or excipient" refers to a carrier and/or excipient that is pharmacologically and/or physiologically compatible with the subject and the active ingredient, is well known in the art (see, for example, Remington's Pharmaceutical Sciences. Edited by Gennaro A R, 19$^{th}$ ed. Pennsylvania: Mack Publishing Company, 1995), and includes, but is not limited to: pH adjusting agents (including but not limited to phosphate buffer), surfactants (including but not limited to cationic, anionic or nonionic surfactants, such as Tween-80), adjuvants, ionic strength enhancers (including but not limited to sodium chloride), diluents, excipients, and medium for containing or administering the therapeutic agent, and any combination thereof.

As used herein, the term "adjuvant" refers to a non-specific immune enhancer, which can enhance the body's immune response to an antigen or change the type of immune response when it is delivered into the body together with the antigen or in advance. Typical examples of adjuvant include, but are not limited to, aluminum adjuvants (e.g., aluminum hydroxide), Freund's adjuvants (e.g., complete Freund's adjuvant and incomplete Freund's adjuvant), *Corynebacterium parvum*, lipopolysaccharides, cytokines, etc.

As used herein, the pharmaceutically acceptable carrier can be a sterile liquid, such as water and oil, including oils derived from petroleum, animal, vegetable or synthesis, such as peanut oil, soybean oil, mineral oil, sesame oil, etc. When the pharmaceutical composition is administered intravenously, water is the preferred carrier. Saline solutions and aqueous dextrose and glycerol solutions can also be used as liquid carriers, especially for injectable solutions.

As used herein, the pharmaceutically acceptable excipient may include starch, glucose, lactose, sucrose, gelatin, malt, rice, flour, chalk, silica gel, sodium stearate, glycerol monostearate, talc, sodium chloride, milk powder, glycerin, propylene, ethylene glycol, water, ethanol, etc. If necessary, the pharmaceutical composition may also contain a wetting agent, or an emulsifying agent such as sodium hyaluronate, or a pH buffering agent. The pharmaceutical composition can be a form of solution, suspension, emulsion, tablet, pill, capsule, powder, sustained-release formulation, etc.

As used herein, the term "effective amount" refers to an amount sufficient to obtain or at least partially obtain the desired effect. For example, a prophylactically effective amount refers to an amount sufficient to prevent, stop or delay the occurrence of a disease; a therapeutically effective amount refers to an amount sufficient to cure or at least partially retard the progression of a disease and its complications in a patient who have already suffered from the disease. It is completely within the abilities of those skilled in the art to determine such an effective amount. For example, the effective amount for therapeutic use will depend on the severity of the disease to be treated, the overall state of the patient's own immune system, the patient's general conditions such as age, weight and sex, the way of administration, other treatments that are simultaneously administered, and so on.

As used herein, the term "subject" refers to a mammal, including but not limited to, human, rodent (mouse, rat, guinea pig), dog, horse, cow, cat, pig, monkey, Chimpanzee and so on. Preferably, the subject is a human.

As used herein, the term "disease that can benefit from the activity of a natural hHGF" refers to a disease in which the enhanced expression and/or activity of HGF can alleviate the symptoms of the disease, retard the progression of the disease, or cure or partially cure the disease.

As previously reported, HGF has a variety of biological activities, including but not limited to one or more of the following activities: (1) promoting the growth and/or migration of endothelial cells; (2) promoting the formation of blood vessels (e.g., microvessels); and/or, (3) promoting the repair of nerve damage (e.g., peripheral neuropathy, such as diabetic peripheral neuropathy). Therefore, HGF may have application prospects in many aspects, including but not limited to: (1) promoting the growth and/or migration of endothelial cells; (2) promoting the formation of blood vessels (e.g., microvascular); (3) treating ischemic diseases, for example, coronary artery disease (CAD) or peripheral artery disease (PAD), such as lower extremity artery ischemia; (4) treating metabolic syndrome and diabetes and complications thereof (e.g., diabetic peripheral neuropathy); (5) inhibiting restenosis; and (6) promoting the repair of nerve damage (e.g., neurodegenerative diseases, traumatic nerve damage, peripheral neuropathy).

Therefore, examples of the term "disease that can benefit from the activity of a natural hHGF" include but are not limited to the above-mentioned diseases, for example, ischemic diseases, metabolic syndromes, diabetes and complications thereof, restenosis, nerve damages, and the like.

The inventors of the present application discovered after research that natural hHGF can be mutated to obtain a hHGF mutant with an enhanced biological activity. Specifically, the inventors of the present application discovered that by mutating the $130^{th}$ amino acid of natural hHGF (with SEQ ID NO:1 as a reference) into an amino acid with a basic side chain (e.g., arginine, histidine, lysine, etc.), the resulting hHGF mutant has stronger biological activity than the natural hHGF. Correspondingly, when the nucleic acid molecule encoding the hHGF mutant is used as a gene therapy drug, it exhibits a stronger therapeutic effect in the subject than the nucleic acid molecule encoding the natural hHGF.

Therefore, in one aspect, the present application provides a mutant of human hepatocyte growth factor (hHGF), which, compared with a natural hHGF, comprises a mutation as follows: the amino acid of the natural hHGF at a position corresponding to the $130^{th}$ position of SEQ ID NO:1 is mutated into an amino acid with a basic side chain.

In certain preferred embodiments, the amino acid with a basic side chain is selected from arginine, histidine and lysine. In certain preferred embodiments, the amino acid with a basic side chain is arginine. In certain preferred embodiments, the amino acid with a basic side chain is histidine. In certain preferred embodiments, the amino acid with a basic side chain is lysine.

In certain preferred embodiments, the natural hHGF has an amino acid sequence as shown in SEQ ID NO:1. In certain preferred embodiments, the natural hHGF is a naturally occurring human hepatocyte growth factor with biological functions, and its amino acid sequence has an identity of at least 85%, at least 90%, at least 95%, at least 96%, at least 97%, at least 98%, or at least 99% as compared with SEQ ID NO:1. In certain preferred embodiments, the natural hHGF is a naturally occurring human hepatocyte growth factor with biological functions, and its amino acid sequence has a difference of one or more (e.g., 1 to 10 or 1 to 5 or 1 to 3) amino acids (e.g., a conservative amino acid substitution) as compared with SEQ ID NO:1.

In certain preferred embodiments, compared with the natural hHGF shown in SEQ ID NO: 1, the mutant comprises the following mutation: the amino acid at the $130^{th}$ position (i.e., serine) of SEQ ID NO: 1 is mutated to arginine. In certain preferred embodiments, the mutant has an amino acid sequence as shown in SEQ ID NO: 2.

In certain preferred embodiments, compared with the natural hHGF shown in SEQ ID NO: 1, the mutant comprises the following mutation: the amino acid at the $130^{th}$ position (i.e., serine) of SEQ ID NO: 1 is mutated to histidine. In certain preferred embodiments, the mutant has an amino acid sequence as shown in SEQ ID NO: 3.

In certain preferred embodiments, compared with the natural hHGF shown in SEQ ID NO: 1, the mutant comprises the following mutation: the amino acid at the $130^{th}$ position (i.e., serine) of SEQ ID NO: 1 is mutated to lysine. In certain preferred embodiments, the mutant has an amino acid sequence as shown in SEQ ID NO:4.

Therefore, in certain preferred embodiments, the mutant has an amino acid sequence selected from SEQ ID NOs: 2, 3 and 4.

It is easy to understand that various modifications can be made to the protein to impart desired properties to the protein. For example, the protein can be modified with polyethylene glycol (PEGylation) to improve the half-life of the protein in vivo. Therefore, in certain preferred embodiments, the mutant is modified. In certain preferred embodiments, the mutant is chemically modified. In certain preferred embodiments, the mutant is modified by PEGylation.

The hHGF mutant of the present application can be prepared by various known methods. In some preferred embodiments, the hHGF mutant is prepared by recombinant expression. In some preferred embodiments, the hHGF mutant is prepared by chemical synthesis. However, it is easy to understand that the hHGF mutant of the present application is not limited by its preparation method.

Compared with a natural hHGF, the hHGF mutant of the present application has stronger biological activity. Without being bound by theory, the inventors of the present application believes that when the amino acid at the $130^{th}$ position (with SEQ ID NO: 1 as a reference) located in the first hairpin structure at the N-terminus of the α chain of natural hHGF is mutated to an amino acid with a basic side chain (e.g., arginine, histidine, lysine), the conformation of the hairpin structure will change, which enhances the binding of hHGF protein to the receptor c-Met, thereby enhancing the biological activity of hHGF protein. Therefore, the hHGF mutant of the present application may exhibit stronger activity in, for example, one or more aspects selected from the following: (1) promoting the growth and/or migration of endothelial cells; (2) promoting the formation of blood vessels (e.g., microvessels); and/or, (3) promoting the repair of nerve damage (e.g., peripheral neuropathy, such as diabetic peripheral neuropathy).

In another aspect, the present application provides an isolated nucleic acid molecule, comprising a nucleotide sequence encoding the mutant of the present invention. In certain preferred embodiments, the nucleic acid molecule encodes a mutant having an amino acid sequence selected from SEQ ID NOs: 2, 3 and 4.

It is easy to understand that the isolated nucleic acid molecule can be used to clone or express the mutant of the present invention. In some cases, in order to improve efficiency, the nucleotide sequence of the nucleic acid molecule can be codon-optimized according to cell preference.

Therefore, in certain preferred embodiments, the nucleotide sequence of the nucleic acid molecule is codon-optimized according to a host cell preference. In certain preferred embodiments, the nucleotide sequence of the nucleic acid molecule is codon-optimized according to CHO cell preference.

In certain preferred embodiments, the nucleic acid molecule has a nucleotide sequence selected from SEQ ID NOs: 6, 7 and 8.

In another aspect, the present application also provides a vector comprising the isolated nucleic acid molecule as described above.

The vector of the present invention can be a cloning vector or an expression vector. In some preferred embodiments, the vector of the present invention can be, for example, a plasmid; a phagemid; a cosmid; an artificial chromosome, such as a yeast artificial chromosome (YAC), a bacterial artificial chromosome (BAC) or an artificial chromosome derived from P1 (PAC); a bacteriophage such as λ bacteriophage or M13 bacteriophage; and a viral vector. Viruses that can be used as the vector include, but are not limited to, retrovirus (including lentivirus), adenovirus, adeno-associated virus, herpes virus (e.g., herpes simplex virus), poxvirus, baculovirus, papillomavirus, papovavirus (e.g., SV40). Therefore, in certain preferred embodiments, the vector of the present invention is a viral vector, such as, but not limited to, a retroviral vector (e.g., a lentiviral vector), an adenovirus vector, an adeno-associated virus vector, a herpes virus vector (e.g., herpes simplex virus vector), a poxvirus vector, a baculovirus vector, a papillomavirus vector, a papovavirus vector. In certain preferred embodiments, the vector of the present invention is selected from adenovirus vector, adeno-associated virus vector, and lentivirus vector.

In certain preferred embodiments, the vector of the present invention can express or be used to express the mutant of the present invention. In certain preferred embodiments, the vector of the present invention can express or be used to express the mutant of the present invention in a subject (e.g., a mammal, such as a human). In certain preferred embodiments, the vector of the present invention is used for gene therapy. In certain preferred embodiments, the vector of the present invention can be used as a gene therapy vector for expressing the mutant of the present invention in a subject (e.g., a mammal, such as a human) and performing gene therapy.

In certain preferred embodiments, the vector of the present invention is a plasmid containing the isolated nucleic acid molecule as described above, such as a naked plasmid. In certain preferred embodiments, the vector of the present invention is a pSN vector containing the isolated nucleic acid molecule as described above. The pSN vector is disclosed in Chinese Patent CN 108611367 B, and has the nucleotide sequence as shown in SEQ ID NO: 9.

In another aspect, the present application also provides a host cell comprising the isolated nucleic acid molecule or the vector of the present invention. Such host cell includes, but is not limited to, a prokaryotic cell such as E. coli cell, and an eukaryotic cell such as yeast cell, insect cell, plant cell and animal cell (e.g., a mammalian cell, such as mouse cell, human cell, etc.). The cell of the present invention can also be a cell line, such as a CHO cell.

In another aspect, the present application also provides a method for preparing the mutant of the present invention, which comprises culturing the host cell of the present invention under a suitable condition, and recovering the mutant of the present invention from a cell culture of the host cell.

In certain preferred embodiments, the method comprises the following steps:
(1) constructing an expression vector, wherein the expression vector comprises a nucleic acid sequence encoding the mutant of the present invention (e.g., the mutant having the amino acid sequence shown in SEQ ID NO: 2, SEQ ID NO: 3 or SEQ ID NO: 4);
(2) introducing the expression vector into a host cell (e.g., a CHO cell), and culturing the host cell under a condition that allows protein expression; and
(3) isolating and recovering the mutant of the present invention from a cell culture of the host cell.

In some preferred embodiments, in step (3), the mutant of the present invention is isolated and recovered by anion exchange chromatography and heparin affinity chromatography.

Compared with a natural hHGF, the hHGF mutant of the present application has stronger biological activity, so that it can be advantageously used as a medicament. Correspondingly, compared with the nucleic acid molecule encoding a natural hHGF, the nucleic acid molecule encoding the hHGF mutant of the present application exhibits a stronger therapeutic effect in the subject, and can also be advantageously used as a medicament. Therefore, in another aspect, the present application also provides a pharmaceutical composition, which comprises the mutant or nucleic acid molecule or vector of the present invention, and optionally, a pharmaceutically acceptable carrier and/or excipient.

In some preferred embodiments, the pharmaceutical composition comprises the mutant of the present invention. In certain preferred embodiments, the mutant is unmodified. In certain preferred embodiments, the mutant is modified, for example, is PEGylated.

In certain preferred embodiments, the pharmaceutical composition is used for gene therapy. In some preferred embodiments, the pharmaceutical composition comprises the nucleic acid molecule or vector of the present invention. In certain preferred embodiments, the vector is a gene therapy vector capable of expressing the mutant of the present invention, such as a plasmid (e.g., a naked plasmid), an adenovirus vector, an adeno-associated virus vector, and a lentivirus vector.

In certain preferred embodiments, the pharmaceutically acceptable carrier and/or excipient is selected from pH adjusters (including but not limited to phosphate buffer), surfactants (including but not limited to cationic, anionic or non-ionic surfactants, such as Tween-80), adjuvants, ionic strength enhancers (including but not limited to sodium chloride), diluents, excipients, media for containing or administering the therapeutic agent, and any combination thereof.

In certain preferred embodiments, the pharmaceutically acceptable carrier may be a sterile liquid, such as water and oil, including oils derived from petroleum, animal, vegetable or synthesis, such as peanut oil, soybean oil, mineral oil, sesame oil and so on. In certain preferred embodiments, the pharmaceutically acceptable carrier is selected from water, saline solution, aqueous dextrose, glycerin, and any combination thereof.

In certain preferred embodiments, the pharmaceutically acceptable excipient may be selected from the group consisting of starch, glucose, lactose, sucrose, gelatin, malt, rice, flour, chalk, silica gel, sodium stearate, glyceryl monostearate, talc, sodium chloride, milk powder, glycerin, propylene, ethylene glycol, water, ethanol, and any combination thereof.

In some preferred embodiments, the pharmaceutical composition may be in the form of solution, suspension, emulsion, tablet, pill, capsule, powder (e.g., lyophilized powder), sustained-release formulation, and the like.

The pharmaceutical composition of the present invention can be administered in various suitable ways. Suitable modes of administration include, but are not limited to, parenteral administration, such as intravenous, intradermal, subcutaneous, oral, intranasal (e.g., inhalation), transdermal (e.g., topical), transmucosal, and rectal administration. In certain preferred embodiments, the pharmaceutical composition is formulated into a pharmaceutical preparation suitable for intravenous, subcutaneous, intramuscular, oral, intranasal, or topical administration to a human according to a conventional procedure.

Generally, the pharmaceutical composition for injection (e.g., intravenous administration, e.g. by bolus injection or continuous infusion) is sterile and isotonic. If necessary, such pharmaceutical composition may also comprise a solubilizer and a local anesthetic such as ergotamine to relieve pain at the injection site. In addition, the pharmaceutical composition for injection may also comprise a preservative. In certain preferred embodiments, the pharmaceutical composition for injection may also be presented in a unit dosage form (e.g., stored in an ampoule or in a multi-dose container).

The pharmaceutical composition for injection may be in the form of suspension, solution, or emulsion in oily or aqueous medium, and may comprise a preparation agent such as suspending agent, stabilizer, and/or dispersing agent. Alternatively, such pharmaceutical composition may also be in a powder form, which is dissolved in a suitable medium (e.g., sterile and pyrogen-free water) before use. In certain preferred embodiments, the pharmaceutical composition is a freeze-dried injection, which comprises 0.01% to 0.2% of the hHGF mutant, 5% of mannitol, and a pharmaceutically acceptable carrier. In some preferred embodiments, the pharmaceutical composition is a freeze-dried injection, which comprises 1 to 10 mg of the nucleic acid molecule or vector according to the present invention, and a pharmaceutically acceptable carrier.

Suitable media that can be used to provide parenteral dosage forms are well known to those skilled in the art. In certain preferred embodiments, the media suitable for parenteral dosage forms include, but are not limited to, water for injection; aqueous media, including, but not limited to, sodium chloride injection, Ringer's injection, glucose injection, glucose and sodium chloride injection, and lactylated Ringer's injection; water miscible media, including, but not limited to, ethanol, polyethylene glycol, and polypropylene glycol; and, non-aqueous media, including, but not limited to, corn oil, cottonseed oil, peanut oil, sesame oil, ethyl oleate, isopropyl myristate, and benzyl benzoate.

Previous studies have shown that HGF can stimulate the growth and migration of endothelial cells (Bussolino et al., J Cell Biol. 119:629 (1992); Nakamura et al., J Hypertens 14:1067 (1996)); and, HGF can be used as a re-endothelialization stimulant (Yasuda et al., Circulation 101: 2546 (2000); Hayashi et al., Gene Ther 7: 1664 (2000)).

It has also been found that HGF can stimulate the formation of a blood vessel by regulating endothelial cell growth and vascular smooth muscle cell migration. Because of its angiogenic activity, HGF is considered as a promising candidate for therapeutic formation of a blood vessel. For example, previous studies reported that HGF can be used to treat ischemic diseases, such as coronary artery disease (CAD) or peripheral artery disease (PAD) (Miyagawa et al., Circulation 105: 2556 (2002); Azuma et al., Gene Ther. 13: 1206 (2006); Aoki et al., Gene Ther. 7:417 (2000); Funatsu et al., J. Thoracic Cardiovasc. Surg. 124: 1099 (2002)).

In addition, it has also been reported that HGF can improve the vascular complications caused by diabetes (Peng et al., 2011), and is used to treat metabolic syndrome and diabetes and complications thereof (e.g., diabetic peripheral neuropathy).

In addition, it has also been reported that HGF can be used as an agent for suppressing restenosis. Studies have shown that rapid endothelial surface reconstruction can inhibit smooth muscle cell proliferation, thereby inhibiting restenosis (Bauters et al., Prog Cardiovasc Dis. 40:107 (1997)). Local delivery of endothelial growth factors (e.g., vascular endothelial growth factor (VEGF) or hepatocyte growth factor (HGF)) to damaged blood vessels has shown the effect of inhibiting restenosis (Asahara et al., Circulation 94:3291 (1996); Yasuda et al., Circulation 101:2546 (2000); Hayashi et al., Gene Ther 7:1664 (2000); Walter et al., Circulation 110:36 (2004)).

It has also been found that HGF is a neurotrophic factor effective in multiple brain regions (Kato et al., 2009; Ebens et al., 1996), which can affect many types of neuronal cells, including motor neurons (Elsen et al., 2009; Hayashi et al., 2006), hippocampal neurons (Lim et al., 2008), cerebellar granule cells (i.e. raci et al., 2002) and sympathetic neurons (1999), and can stimulate at the same time the neurogenesis and synaptogenesis (Shang et al., 2011; Wang et al, 2011). It has been reported that HGF/c-Met signal transduction can promote the wound healing of neurons (Trappal et al., 2008), especially after local ischemic brain injury (Takeo et al., 2007). It has also been reported that the administration of hepatocyte growth factor (HGF) in murine or rat models with familial amyotrophic lateral sclerosis (ALS) disease can significantly slow down the degeneration of motor neurons (Aoki et al., 2009); reduce the glial proliferation that contributes to the degenerative process (Kadoyama et al., 2007); delay the onset of paralysis (Kadayama et al., 2009); and increase life span (Sun et al., 2002). These findings indicate that HGF has therapeutic and neuroprotective effects in a variety of neurological diseases, such as neurodegenerative diseases (e.g., ALS, Parkinson's disease, dementia), traumatic brain injury, and traumatic spinal cord injury.

Therefore, HGF has been shown to have application prospects in many aspects, including: (1) promoting the growth and/or migration of endothelial cells; (2) promoting the formation of blood vessels (e.g., microvessels); (3) treating ischemic diseases, such as coronary artery disease (CAD) or peripheral artery disease (PAD), such as lower extremity artery ischemia; (4) treatment of metabolic syndrome and diabetes and complications thereof (e.g., diabetic peripheral neuropathy); (5) inhibiting restenosis; and (6) promoting the repair of nerve damage (e.g., neurodegenerative diseases, traumatic nerve damage, peripheral neuropathy). The hHGF mutant of the present application has stronger biological activity than a natural hHGF, and thus can be advantageously used in the above-mentioned applications.

Therefore, in another aspect, the present application provides a method for treating a disease that can benefit from the activity of a natural hHGF in a subject, which comprises administering to the subject in need thereof a therapeutically effective amount of the mutant or nucleic acid molecule or vector or pharmaceutical composition according to the present invention.

In certain preferred embodiments, the disease is selected from ischemic diseases, metabolic syndrome, diabetes and complications thereof, restenosis, and nerve damage. In certain preferred embodiments, the disease is an ischemic disease, such as coronary artery disease (CAD) or peripheral artery disease (PAD), such as myocardial infarction or lower extremity artery ischemia. In certain preferred embodiments, the disease is diabetes or a complication thereof, such as diabetic peripheral neuropathy. In certain preferred embodiments, the disease is restenosis, such as restenosis after surgery and restenosis after perfusion. In certain preferred embodiments, the disease is nerve damage, such as neurodegenerative disease (e.g., amyotrophic lateral sclerosis (ALS), Parkinson's disease, dementia), traumatic nerve damage, peripheral neuropathy (e.g., diabetic peripheral neuropathy). In certain preferred embodiments, the disease is selected from the group consisting of lower extremity artery ischemia, myocardial infarction, and diabetic peripheral neuropathy.

In certain preferred embodiments, a therapeutically effective amount of the mutant of the present invention is administered to a subject in need thereof, thereby treating the disease (e.g., lower extremity artery ischemia, myocardial infarction, and/or diabetic peripheral neuropathy). In certain preferred embodiments, the mutant is unmodified. In certain preferred embodiments, the mutant is modified, for example, is PEGylated.

In certain preferred embodiments, a therapeutically effective amount of the nucleic acid molecule or vector of the present invention is administered to a subject in need thereof, thereby treating the subject's disease (e.g., lower extremity artery ischemia, myocardial ischemia, myocardial infarction and/or diabetic peripheral neuropathy). In certain preferred embodiments, the vector is a gene therapy vector capable of expressing the mutant of the present invention, such as a plasmid (e.g., a naked plasmid), an adenovirus vector, an adeno-associated virus vector, and a lentivirus vector.

Those of ordinary skill in the art know that the mode, frequency and dosage of the administration will vary depending on the disorder, condition and individual being treated. Generally, the administration can be performed by injection (e.g., intradermal, intramuscular, intravenous, or subcutaneous), topical administration (e.g., epidermal administration), or drip administration. In addition, it is also possible to select a reasonable administration route and administration scheme according to individual patient. A suitable dose is an amount that can effectively treat the disease (e.g., lower extremity artery ischemia, myocardial infarction, and/or diabetic peripheral neuropathy) after administration of the above-mentioned pharmaceutical composition.

For the pharmaceutical composition containing the mutant of the present invention, the amount of the active ingredient contained in the unit dosage form may be, for example, about 10 μg to 5 mg. The appropriate dosage will vary depending on the patient's condition and the mode of administration, and may be, for example, about 1 μg to 100 μg/kg body weight.

For the pharmaceutical composition containing the nucleic acid molecule or vector of the present invention, the amount of the active ingredient contained in the unit dosage form can be, for example, about 1 to 10 mg. The appropriate dosage will vary depending on the patient's condition and the mode of administration, and may be, for example, about 10 to 200 μg/kg body weight.

In another aspect, the present application provides a use of the mutant or nucleic acid molecule or vector of the present invention in the manufacture of a pharmaceutical composition for the treatment of a disease in a subject that can benefit from the activity of natural hHGF.

In certain preferred embodiments, the disease is selected from the group consisting of ischemic disease, metabolic syndrome, diabetes and complications thereof, restenosis, and nerve damage. In some preferred embodiments, the disease is an ischemic disease, such as coronary artery disease (CAD) or peripheral artery disease (PAD), such as myocardial infarction or lower extremity artery ischemia. In certain preferred embodiments, the disease is diabetes or complication thereof, such as diabetic peripheral neuropathy. In certain preferred embodiments, the disease is restenosis, such as restenosis after surgery and restenosis after perfusion. In certain preferred embodiments, the disease is nerve damage, such as neurodegenerative disease (e.g., amyotrophic lateral sclerosis (ALS), Parkinson's disease, dementia), traumatic nerve damage, peripheral neuropathy (e.g., diabetic peripheral neuropathy). In certain preferred embodiments, the disease is selected from the group consisting of lower extremity artery ischemia, myocardial infarction, and diabetic peripheral neuropathy.

In some preferred embodiments, the pharmaceutical composition comprises the mutant of the present invention. In certain preferred embodiments, the mutant is unmodified. In certain preferred embodiments, the mutant is modified, for example, is PEGylated.

In certain preferred embodiments, the pharmaceutical composition is used for gene therapy. In some preferred embodiments, the pharmaceutical composition comprises the nucleic acid molecule or vector of the present invention. In certain preferred embodiments, the vector is a gene therapy vector capable of expressing the mutant of the present invention, such as a plasmid (e.g., a naked plasmid), an adenovirus vector, an adeno-associated virus vector, and a lentivirus vector.

In another aspect, provided is the mutant or nucleic acid molecule or vector or pharmaceutical composition of the present invention for use in the treatment of a disease in a subject that can benefit from the activity of natural hHGF.

In certain preferred embodiments, the disease is selected from the group consisting of ischemic disease, metabolic syndrome, diabetes and complications thereof, restenosis, and nerve damage. In certain preferred embodiments, the disease is an ischemic disease, such as coronary artery disease (CAD) or peripheral artery disease (PAD), such as myocardial infarction or lower extremity artery ischemia. In certain preferred embodiments, the disease is diabetes or complication thereof, such as diabetic peripheral neuropathy. In certain preferred embodiments, the disease is restenosis, such as restenosis after surgery and restenosis after perfusion. In certain preferred embodiments, the disease is nerve damage, such as neurodegenerative diseases (e.g., amyotrophic lateral sclerosis (ALS), Parkinson's disease, dementia), traumatic nerve damage, peripheral neuropathy (e.g., diabetic peripheral neuropathy). In certain preferred embodiments, the disease is selected from the group consisting of lower extremity artery ischemia, myocardial infarction, and diabetic peripheral neuropathy.

In certain preferred embodiments, the mutant is unmodified. In certain preferred embodiments, the mutant is modified, for example, is PEGylated. In certain preferred embodiments, the nucleic acid molecule or vector is used for gene therapy. In certain preferred embodiments, the vector is a gene therapy vector capable of expressing the mutant of the present invention, such as a plasmid (e.g., a naked plasmid), an adenovirus vector, an adeno-associated virus vector, and a lentivirus vector.

In another aspect, the present application provides a method for promoting the growth and/or migration of an endothelial cell, which comprises administering an effective amount of the mutant or nucleic acid molecule or vector or pharmaceutical composition of the present invention to an endothelial cell or subject in need thereof.

In certain preferred embodiments, the method is used in vivo. For example, the mutant or nucleic acid molecule or vector or pharmaceutical composition of the present invention can be administered to a subject to promote the growth and/or migration of an endothelial cell in the subject. In certain preferred embodiments, the method is used in vitro. For example, the mutant or nucleic acid molecule or vector or pharmaceutical composition of the present invention can be administered to an endothelial cell cultured in vitro to promote the growth and/or migration of the endothelial cell in culture. In certain preferred embodiments, the endothelial cell is an umbilical vein endothelial cell.

In another aspect, the present application provides a method for promoting the formation of a blood vessel, which comprises administering an effective amount of the mutant or nucleic acid molecule or vector or pharmaceutical composition of the present invention to a subject in need thereof. In certain preferred embodiments, the formation of a blood vessel is the formation of a microvessel.

In another aspect, the present application provides a use of the mutant or nucleic acid molecule or vector of the present invention in the manufacture of a pharmaceutical composition, the pharmaceutical composition is used for promoting the growth and/or migration of an endothelial cell or promoting the formation of a blood vessel. In certain preferred embodiments, the endothelial cell is an umbilical vein endothelial cell. In certain preferred embodiments, the formation of a blood vessel is the formation of a microvessel.

In another aspect, provided is the mutant or nucleic acid molecule or vector or pharmaceutical composition of the present invention for use in promoting the growth and/or migration of an endothelial cell or promoting the formation of a blood vessel. In certain preferred embodiments, the endothelial cell is an umbilical vein endothelial cell. In certain preferred embodiments, the formation of a blood vessel is the formation of a microvessel.

Beneficial Effects of the Present Invention

Compared with a natural hHGF, the hHGF mutant of the present application has stronger biological activity. In particular, the inventors of the present application have discovered through researches that the hHGF mutant of the present invention can exhibit stronger biological activity in, for example, the following aspects: (1) promoting the growth and/or migration of endothelial cells; (2) promoting the formation of blood vessels (e.g., microvessels); and/or, (3) promoting the repair of nerve damage (e.g., peripheral neuropathy, such as diabetic peripheral neuropathy).

Therefore, the hHGF mutant and the nucleic acid molecule encoding the hHGF mutant of the present invention can be more beneficially applied to one or more of the following aspects: (1) promoting the growth and/or migration of endothelial cells; (2) promoting the formation of blood vessels (e.g., microvessels); (3) treating ischemic diseases, such as coronary artery disease (CAD) or peripheral artery disease (PAD), such as lower extremity artery ischemia; (4) treating metabolic syndrome and diabetes and complications thereof (e.g., diabetic peripheral neuropathy); (5) inhibiting restenosis; and (6) promoting the repair of nerve damage (e.g., neurodegenerative diseases, traumatic nerve injury, peripheral neuropathy).

The embodiments of the present application will be described in detail below with reference to the drawings and examples. However, those skilled in the art will understand that the following drawings and examples are only used to illustrate the present application, and not to limit the scope of the present application. According to the accompanying drawings and the following detailed description of the preferred embodiments, various objects and advantageous aspects of the present application will become apparent to those skilled in the art.

BRIEF DESCRIPTION OF THE DRAWINGS

FIG. 1 shows the SD S-PAGE detection results of the four target proteins prepared in Example 1 (i.e., natural hHGF, 130Arg-hHGF, 130His-hHGF and 130Lys-hHGF), in which Lane 1: natural hHGF; Lane 2: 130Arg-hHGF; Lane 3: 130His-hHGF; Lane 4: 130Lys-hHGF; Lane 5: protein molecular weight marker.

DESCRIPTION OF SEQUENCE INFORMATION

The information of the sequences involved in the present invention is provided as follows.

```
SEQ ID NO: 1 (amino acid sequence of natural hHGF)
QRKRRNTIHEFKKSAKTTLIKIDPALKIKTKKVNTADQCANRCTRNKGLPFTCKAFVFDKARKQC

LWFPFNSMSSGVKKEFGHEFDLYENKDYIRNCIIGKGRSYKGTVSITKSGIKCQPWSSMIPHEHSF

LPSSYRGKDLQENYCRNPRGEEGGPWCFTSNPEVRYEVCDIPQCSEVECMTCNGESYRGLMDHT

ESGKICQRWDHQTPHRHKFLPERYPDKGFDDNYCRNPDGQPRPWCYTLDPHTRWEYCAIKTCA

DNTMNDTDVPLETTECIQGQGEGYRGTVNTIWNGIPCQRWDSQYPHEHDMTPENFKCKDLREN

YCRNPDGSESPWCFTTDPNIRVGYCSQIPNCDMSHGQDCYRGNGKNYMGNLSQTRSGLTCSMW

DKNMEDLHRHIFWEPDASKLNENYCRNPDDDAHGPWCYTGNPLIPWDYCPISRCEGDTTPTIVN

LDHPVISCAKTKQLRVVNGIPTRTNIGWMVSLRYRNKHICGGSLIKESWVLTARQCFPSRDLKDY

EAWLGIHDVHGRGDEKCKQVLNVSQLVYGPEGSDLVLMKLARPAVLDDFVSTIDLPNYGCTIPE
```

-continued

KTSCSVYGWYTGLINYDGLLRVAHLYIMGNEKCSQHHRGKVTLNESEICAGAEKIGSGPCEGD

YGGPLVCEQHKMRMVLGVIVPGRGCAIPNRPGIFVRVAYYAKWIHKIILTYKVPQS

SEQ ID NO: 2 (amino acid sequence of 130Arg-hHGF)
QRKRRNTIHEFKKSAKTTLIKIDPALKIKTKKVNTADQCANRCTRNKGLPFTCKAFVFDKARKQC

LWFPFNSMSSGVKKEFGHEFDLYENKDYIRNCIIGKGRSYKGTVSITKSGIKCQPWSSMIPHEHRF

LPSSYRGKDLQENYCRNPRGEEGGPWCFTSNPEVRYEVCDIPQCSEVECMTCNGESYRGLMDHT

ESGKICQRWDHQTPHRHKFLPERYPDKGFDDNYCRNPDGQPRPWCYTLDPHTRWEYCAIKTCA

DNTMNDTDVPLETTECIQGQGEGYRGTVNTIWNGIPCQRWDSQYPHEHDMTPENFKCKDLREN

YCRNPDGSESPWCFTTDPNIRVGYCSQIPNCDMSHGQDCYRGNGKNYMGNLSQTRSGLTCSMW

DKNMEDLHRHIFWEPDASKLNENYCRNPDDDAHGPWCYTGNPLIPWDYCPISRCEGDTTPTIVN

LDHPVISCAKTKQLRVVNGIPTRTNIGWMVSLRYRNKHICGGSLIKESWVLTARQCFPSRDLKDY

EAWLGIHDVHGRGDEKCKQVLNVSQLVYGPEGSDLVLMKLARPAVLDDFVSTIDLPNYGCTIPE

KTSCSVYGWYTGLINYDGLLRVAHLYIMGNEKCSQHHRGKVTLNESEICAGAEKIGSGPCEGD

YGGPLVCEQHKMRMVLGVIVPGRGCAIPNRPGIFVRVAYYAKWIHKIILTYKVPQS

SEQ ID NO: 3 (amino acid sequence of 130His-hHGF)
QRKRRNTIHEFKKSAKTTLIKIDPALKIKTKKVNTADQCANRCTRNKGLPFTCKAFVFDKARKQC

LWFPFNSMSSGVKKEFGHEFDLYENKDYIRNCIIGKGRSYKGTVSITKSGIKCQPWSSMIPHEHHF

LPSSYRGKDLQENYCRNPRGEEGGPWCFTSNPEVRYEVCDIPQCSEVECMTCNGESYRGLMDHT

ESGKICQRWDHQTPHRHKFLPERYPDKGFDDNYCRNPDGQPRPWCYTLDPHTRWEYCAIKTCA

DNTMNDTDVPLETTECIQGQGEGYRGTVNTIWNGIPCQRWDSQYPHEHDMTPENFKCKDLREN

YCRNPDGSESPWCFTTDPNIRVGYCSQIPNCDMSHGQDCYRGNGKNYMGNLSQTRSGLTCSMW

DKNMEDLHRHIFWEPDASKLNENYCRNPDDDAHGPWCYTGNPLIPWDYCPISRCEGDTTPTIVN

LDHPVISCAKTKQLRVVNGIPTRTNIGWMVSLRYRNKHICGGSLIKESWVLTARQCFPSRDLKDY

EAWLGIHDVHGRGDEKCKQVLNVSQLVYGPEGSDLVLMKLARPAVLDDFVSTIDLPNYGCTIPE

KTSCSVYGWYTGLINYDGLLRVAHLYIMGNEKCSQHHRGKVTLNESEICAGAEKIGSGPCEGD

YGGPLVCEQHKMRMVLGVIVPGRGCAIPNRPGIFVRVAYYAKWIHKIILTYKVPQS

SEQ ID NO: 4 (amino acid sequence of 130Lys-hHGF)
QRKRRNTIHEFKKSAKTTLIKIDPALKIKTKKVNTADQCANRCTRNKGLPFTCKAFVFDKARKQC

LWFPFNSMSSGVKKEFGHEFDLYENKDYIRNCIIGKGRSYKGTVSITKSGIKCQPWSSMIPHEHKF

LPSSYRGKDLQENYCRNPRGEEGGPWCFTSNPEVRYEVCDIPQCSEVECMTCNGESYRGLMDHT

ESGKICQRWDHQTPHRHKFLPERYPDKGFDDNYCRNPDGQPRPWCYTLDPHTRWEYCAIKTCA

DNTMNDTDVPLETTECIQGQGEGYRGTVNTIWNGIPCQRWDSQYPHEHDMTPENFKCKDLREN

YCRNPDGSESPWCFTTDPNIRVGYCSQIPNCDMSHGQDCYRGNGKNYMGNLSQTRSGLTCSMW

DKNMEDLHRHIFWEPDASKLNENYCRNPDDDAHGPWCYTGNPLIPWDYCPISRCEGDTTPTIVN

LDHPVISCAKTKQLRVVNGIPTRTNIGWMVSLRYRNKHICGGSLIKESWVLTARQCFPSRDLKDY

EAWLGIHDVHGRGDEKCKQVLNVSQLVYGPEGSDLVLMKLARPAVLDDFVSTIDLPNYGCTIPE

KTSCSVYGWYTGLINYDGLLRVAHLYIMGNEKCSQHHRGKVTLNESEICAGAEKIGSGPCEGD

YGGPLVCEQHKMRMVLGVIVPGRGCAIPNRPGIFVRVAYYAKWIHKIILTYKVPQS

SEQ ID NO: 5 (nucleotide sequence encoding natural hHGF)
caaaggaaaa aagagaaatac aattcatgaa ttcaaaaaat cagcaaagac taccctaatc    60
aaaatagatc cagcactgaa gataaaaacc aaaaagtga atactgcaga ccaatgtgct   120
aatagatgta ctaggaataa aggcttcca ttcacttgca aggcttttgt ttttgataaa   180
gcaagaaaac aatgcctctg gttccccttc aatagcatgt caagtggagt gaaaaaagaa   240

-continued

```
tttggccatg aatttgacct ctatgaaaac aaagactaca ttagaaactg catcattggt    300
aaaggacgca gctacaaggg aacagtatct atcactaaga gtggcatcaa atgtcagccc    360
tggagttcca tgataccaca cgaacacagc ttttttgcctt cgagctatcg gggtaaagac   420
ctacaggaaa actactgtcg aaatcctcga ggggaagaag ggggaccctg tgtttcaca     480
agcaatccag aggtacgcta cgaagtctgt gacattcctc agtgttcaga agttgaatgc    540
atgacctgca atggggagag ttatcgaggt ctcatggatc atacagaatc aggcaagatt    600
tgtcagcgct gggatcatca gacaccacac cggcacaaat tcttgcctga agatatccc    660
gacaagggct tgatgataa ttattgccgc aatcccgatg ccagccgag gccatggtgc      720
tatactcttg accctcacac ccgctgggag tactgtgcaa ttaaaacatg cgctgacaat    780
actatgaatg acactgatgt tccttttggaa acaactgaat gcatccaagg tcaaggagaa   840
ggctacaggg gcactgtcaa taccatttgg aatggaattc catgtcagcg ttgggattct    900
cagtatcctc acgagcatga catgactcct gaaaatttca gtgcaagga cctacgaaa     960
aattactgcc gaaatccaga tgggtctgaa tcaccctggt gttttaccac tgatccaaac   1020
atccgagttg gctactgctc ccaaattcca actgtgata tgtcacatgg acaagattgt    1080
tatcgtggga atggcaaaaa ttatatgggc aacttatccc aaacaagatc tggactaaca   1140
tgttcaatgt gggacaagaa catggaagac ttacatcgtc atatcttctg ggaaccagat   1200
gcaagtaagc tgaatgagaa ttactgccga aatccagatg atgatgctca tggaccctgg   1260
tgctacacgg gaaatccact cattccttgg gattattgcc ctatttctcg ttgtgaaggt   1320
gataccacac ctacaatagt caatttagac catcccgtaa tatcttgtgc caaaacgaaa   1380
caattgcgag ttgtaaatgg gattccaaca cgaacaaaca taggatggat ggttagtttg   1440
agatacagaa ataaacatat ctgcggagga tcattgataa aggagagttg ggttcttact   1500
gcacgacagt gtttccttc tcgagacttg aaagattatg aagcttggct tggaattcat   1560
gatgtccacg gaagaggaga tgagaaatgc aaacaggttc tcaatgtttc ccagctggta   1620
tatggccctg aaggatcaga tctggtttta atgaagcttg ccaggcctgc tgtcctggat   1680
gatttttgtta gtacgattga tttacctaat tatggatgca caattcctga aaagaccagt   1740
tgcagtgttt atggctgggg ctacactgga ttgatcaact atgatggcct attacgagtg   1800
gcacatctct atataatggg aaatgagaaa tgcagccagc atcatcgagg aaggtgact    1860
ctgaatgagt ctgaaatatg tgctgggct gaaaagattg gatcaggacc atgtgagggg   1920
gattatggtg gcccacttgt ttgtgagcaa cataaaatga aatggttct tggtgtcatt    1980
gttcctggtc gtggatgtgc cattccaaat cgtcctggta tttttgtccg agtagcatat   2040
tatgcaaaat ggatacacaa aattatttta acatataagg taccacagtc atag         2094
```
SEQ ID NO: 6 (nucleotide sequence encoding 130Arg-hHGF)
```
caaaggaaaa gaagaaatac aattcatgaa ttcaaaaaat cagcaaagac taccctaatc     60
aaaatagatc cagcactgaa gataaaaacc aaaaaagtga atactgcaga ccaatgtgct    120
aatagatgta ctaggaataa aggacttcca ttcacttgca aggcttttgt ttttgataaa    180
gcaagaaaac aatgcctctg gttcccccttc aatagcatgt caagtggagt gaaaaaagaa   240
tttggccatg aatttgacct ctatgaaaac aaagactaca ttagaaactg catcattggt    300
aaaggacgca gctacaaggg aacagtatct atcactaaga gtggcatcaa atgtcagccc    360
tggagttcca tgataccaca cgaacacaga ttttttgcctt cgagctatcg gggtaaagac   420
ctacaggaaa actactgtcg aaatcctcga ggggaagaag ggggaccctg tgtttcaca    480
agcaatccag aggtacgcta cgaagtctgt gacattcctc agtgttcaga agttgaatgc    540
```

-continued

```
atgacctgca atgggagag ttatcgaggt ctcatggatc atacagaatc aggcaagatt    600
tgtcagcgct gggatcatca gacaccacac cggcacaaat tcttgcctga agatatccc    660
gacaagggct tgatgataa ttattgccgc aatcccgatg ccagccgag gccatggtgc    720
tatactcttg accctcacac ccgctgggag tactgtgcaa ttaaaacatg cgctgacaat    780
actatgaatg acactgatgt tcctttggaa caactgaat gcatccaagg tcaaggagaa    840
ggctacaggg gcactgtcaa taccatttgg aatggaattc catgtcagcg ttgggattct    900
cagtatcctc acgagcatga catgactcct gaaaatttca gtgcaagga cctacgagaa    960
aattactgcc gaaatccaga tgggtctgaa tcaccctggt gttttaccac tgatccaaac   1020
atccgagttg gctactgctc ccaaattcca aactgtgata tgtcacatgg acaagattgt   1080
tatcgtggga atggcaaaaa ttatatgggc aacttatccc aaacaagatc tggactaaca   1140
tgttcaatgt gggacaagaa catggaagac ttacatcgtc atatcttctg gaaccagat   1200
gcaagtaagc tgaatgagaa ttactgccga atccagatg atgatgctca tggaccctgg   1260
tgctacacgg gaaatccact cattccttgg gattattgcc ctatttctcg ttgtgaaggt   1320
gataccacac ctacaatagt caatttagac catcccgtaa tatcttgtgc caaaacgaaa   1380
caattgcgag ttgtaaatgg gattccaaca cgaacaaaca taggatggat ggttagtttg   1440
agatacagaa ataaacatat ctgcggagga tcattgataa aggagagttg ggttcttact   1500
gcacgacagt gtttccttc tcgagacttg aaagattatg aagcttggct tggaattcat   1560
gatgtccacg gaagaggaga tgagaaatgc aaacaggttc tcaatgtttc ccagctggta   1620
tatgccctg aaggatcaga tctggtttta atgaagcttg ccaggcctgc tgtcctggat   1680
gattttgtta gtacgattga tttacctaat tatggatgca caattcctga aaagaccagt   1740
tgcagtgttt atggctgggg ctacactgga ttgatcaact atgatggcct attacgagtg   1800
gcacatctct atataatggg aaatgagaaa tgcagccagc atcatcgagg aaggtgact   1860
ctgaatgagt ctgaaatatg tgctggggct gaaaagattg gatcaggacc atgtgagggg   1920
gattatggtg gcccacttgt ttgtgagcaa cataaaatga aatggttct tggtgtcatt   1980
gttcctggtc gtgatgtgc cattccaaat cgtcctggta tttttgtccg agtagcatat   2040
tatgcaaaat ggatacacaa aattatttta acatataagg taccacagtc atag       2094
SEQ ID NO: 7 (nucleotide sequence encoding 130His-hHGF)
caaaggaaaa gaagaaatac aattcatgaa ttcaaaaaat cagcacaaagac tacccctaatc    60
aaaatagatc cagcactgaa gataaaaacc aaaaaagtga atactgcaga ccaatgtgct   120
aatagatgta ctaggaataa aggacttcca ttcacttgca aggcttttgt ttttgataaa   180
gcaagaaaac aatgcctctg ttccccttc aatagcatgt caagtggagt gaaaaagaa   240
tttggccatg aatttgacct ctatgaaaac aaagactaca ttagaaactg catcattggt   300
aaaggacgca gctacaaggg aacagtatct atcactaaga gtggcatcaa atgtcagccc   360
tggagttcca tgataccaca cgaacaccac ttttttgcctt cgagctatcg gggtaaagac   420
ctacaggaaa actactgtcg aaatcctcga ggggaagaag ggggaccctg tgtttcaca    480
agcaatccag aggtacgcta cgaagtctgt gacattcctc agtgttcaga agttgaatgc   540
atgacctgca atgggagag ttatcgaggt ctcatggatc atacagaatc aggcaagatt    600
tgtcagcgct gggatcatca gacaccacac cggcacaaat tcttgcctga agatatccc    660
gacaagggct tgatgataa ttattgccgc aatcccgatg ccagccgag gccatggtgc    720
tatactcttg accctcacac ccgctgggag tactgtgcaa ttaaaacatg cgctgacaat    780
actatgaatg acactgatgt tcctttggaa caactgaat gcatccaagg tcaaggagaa    840
```

```
ggctacaggg gcactgtcaa taccatttgg aatggaattc catgtcagcg ttgggattct   900
cagtatcctc acgagcatga catgactcct gaaaatttca agtgcaagga cctacgagaa   960
aattactgcc gaaatccaga tgggtctgaa tcaccctggt gttttaccac tgatccaaac  1020
atccgagttg gctactgctc ccaaattcca aactgtgata tgtcacatgg acaagattgt  1080
tatcgtggga atggcaaaaa ttatatgggc aacttatccc aaacaagatc tggactaaca  1140
tgttcaatgt gggacaagaa catggaagac ttacatcgtc atatcttctg gaaccagat   1200
gcaagtaagc tgaatgagaa ttactgccga aatccagatg atgatgctca ggaccctgg   1260
tgctacacgg gaaatccact cattccttgg gattattgcc ctatttctcg ttgtgaaggt  1320
gataccacac ctacaatagt caatttagac catcccgtaa tatcttgtgc caaaacgaaa  1380
caattgcgag ttgtaaatgg gattccaaca cgaacaaaca taggatggat ggttagtttg  1440
agatacagaa ataaacatat ctgcggagga tcattgataa aggagagttg ggttcttact  1500
gcacgacagt gtttcccttc tcgagacttg aaagattatg aagcttggct tggaattcat  1560
gatgtccacg aagaggaga tgagaaatgc aaacaggttc tcaatgtttc ccagctggta  1620
tatgccctg aaggatcaga tctggtttta atgaagcttg ccaggcctgc tgtcctggat  1680
gattttgtta gtacgattga tttacctaat tatggatgca caattcctga aaagaccagt  1740
tgcagtgttt atggctgggg ctacactgga ttgatcaact atgatggcct attacgagtg  1800
gcacatctct atataatggg aaatgagaaa tgcagccagc atcatcgagg aaggtgact   1860
ctgaatgagt ctgaaatatg tgctggggct gaaagattg gatcaggacc atgtgagggg   1920
gattatggtg gcccacttgt ttgtgagcaa cataaaatga aatggttct tggtgtcatt   1980
gttcctggtc gtggatgtgc cattccaaat cgtcctggta ttttttgtccg agtagcatat  2040
tatgcaaaat ggatacacaa aattattta acatataagg taccacagtc atag         2094
SEQ ID NO: 8 (nucleotide sequence encoding 130Lys-hHGF)
caaaggaaaa gaagaaatac aattcatgaa ttcaaaaaat cagcaaagac taccctaatc    60
aaaatagatc cagcactgaa gataaaaacc aaaaaagtga atactgcaga ccaatgtgct   120
aatagatgta ctaggaataa aggcttcca ttcacttgca aggcttttgt ttttgataaa   180
gcaagaaaac aatgcctctg gttccccttc aatagcatgt caagtggagt gaaaaaagaa   240
tttggccatg aatttgacct ctatgaaaac aaagactaca ttagaaactg catcattggt   300
aaaggacgca gctacaaggg aacagtatct atcactaaga gtggcatcaa atgtcagccc   360
tggagttcca tgataccaca cgaacacaag ttttttgcctt cgagctatcg gggtaaagac   420
ctacaggaaa actactgtcg aaatcctcga ggggaagaag ggggaccctg tgtttcaca   480
agcaatccag aggtacgcta cgaagtctgt gacattcctc agtgttcaga gttgaatgc   540
atgacctgca tggggagag ttatcgaggt ctcatggatc atacagaatc aggcaagatt   600
tgtcagcgct gggatcatca gacaccacac cggcacaaat tcttgcctga agatatccc   660
gacaagggct ttgatgataa ttattgccgc aatcccgatg ccagccgag gccatggtgc   720
tatactcttg accctcacac ccgctgggag tactgtgcaa ttaaaacatg cgctgacaat   780
actatgaatg acactgatgt tccttttggaa acaactgaat gcatccaagg tcaaggagaa   840
ggctacaggg gcactgtcaa taccatttgg aatggaattc catgtcagcg ttgggattct   900
cagtatcctc acgagcatga catgactcct gaaaatttca agtgcaagga cctacgagaa   960
aattactgcc gaaatccaga tgggtctgaa tcaccctggt gttttaccac tgatccaaac  1020
atccgagttg gctactgctc ccaaattcca aactgtgata tgtcacatgg acaagattgt  1080
tatcgtggga atggcaaaaa ttatatgggc aacttatccc aaacaagatc tggactaaca  1140
```

-continued

```
tgttcaatgt gggacaagaa catggaagac ttacatcgtc atatcttctg ggaaccagat   1200
gcaagtaagc tgaatgagaa ttactgccga aatccagatg atgatgctca tggaccctgg   1260
tgctacacgg gaaatccact cattccttgg gattattgcc ctatttctcg ttgtgaaggt   1320
gataccacac ctacaatagt caatttagac catcccgtaa tatcttgtgc caaaacgaaa   1380
caattgcgag ttgtaaatgg gattccaaca cgaacaaaca taggatggat ggttagtttg   1440
agatacagaa ataaacatat ctgcggagga tcattgataa aggagagttg ggttcttact   1500
gcacgacagt gtttcccttc tcgagacttg aaagattatg aagcttggct tggaattcat   1560
gatgtccacg gaagaggaga tgagaaatgc aaacaggttc tcaatgtttc ccagctggta   1620
tatggccctg aaggatcaga tctggttttta atgaagcttg ccaggcctgc tgtcctggat   1680
gattttgtta gtacgattga tttacctaat tatggatgca caattcctga aaagaccagt   1740
tgcagtgttt atggctgggg ctacactgga ttgatcaact atgatggcct attacgagtg   1800
gcacatctct atataatggg aaatgagaaa tgcagccagc atcatcgagg gaaggtgact   1860
ctgaatgagt ctgaaatatg tgctggggct gaaaagattg gatcaggacc atgtgagggg   1920
gattatggtg gcccacttgt ttgtgagcaa cataaaatga gaatggttct tggtgtcatt   1980
gttcctggtc gtggatgtgc cattccaaat cgtcctggta ttttttgtccg agtagcatat   2040 tatgcaaaat ggatacacaa aattatttta acatataagg taccacagtc atag           2094

SEQ ID NO: 9 (nucleotide sequence of pSN vector)
gcgcagcacc atggcctgaa ataacctctg aaagaggaac ttggttaggt accttctgag     60
gcggaaagaa ccagctgtgg aatgtgtgtc agttagggtg tggaaagtcc ccaggctccc    120
cagcaggcag aagtatgcaa agcatgcatc tcaattagtc agcaaccagg tgtggaaagt    180
ccccaggctc cccagcaggc agaagtatgc aaagcatgca tctcaattag tcagcaacca    240
tagtcccgcc cctaactccg cccatcccgc cctaactccg cccagttccg cccattctc     300 cgccccatgg ctgactaatt ttttttattt atgcagaggc cgaggccgcc tcggcctctg    360
agctattcca gaagtagtga ggaggctttt ttggaggcct aggcttttgc aaaaagcttg    420
ctagccaccg cggccgcaac ttgtttattg cagcttataa tggttacaaa taaagcaata    480
gcatcacaaa tttcacaaat aaagcatttt tttcactgca ttctagttgt ggtttgtcca    540
aactcatcaa tgtatcttat catgtctgga tccaggataa tatatggtag ggttcatagc    600
cagagtaacc tttttttta atttttattt tatttttattt tgagctgcag gcatgcaagc    660
tggcactggc cgtcgtttta caacgtcgtg actgggaaaa ccctggcgtt acccaactta    720
atcgccttgc agcacatccc cctttcgcca gctggcgtaa tagcgaagag gcccgcaccg    780 atcgccctc ccaacagttg cgcagcctga atggcgaatg gcgcctgatg cggtattttc    840
tccttacgca tctgtgcggt atttcacacc gcatatggtg cactctcagt acaatctgct    900
ctgatgccgc atagttaagc cagccccgac acccgccaac acccgctgac gcgccctgac    960
gggcttgtct gctcccggca tccgcttaca acaagctgt gaccgtctcc gggagctgca   1020
tgtgtcagag gttttcaccg tcatcaccga aacgcgcgag acgaaagggc ctcgtgatac   1080
gcctattttt ataggttaat gtcatgataa taatggtttc ttagacgtca ggtggcactt   1140
ttcggggaaa tgtgcgcgga acccctattt gtttatttttt ctaaatacat tcaaatatgt   1200
atccgctcat gagacaataa ccctgataaa tgcttcaata atattgaaaa aggaagagta   1260
tgctggggag tcgaaattca gaagaactcg tcaagaaggc gatagaaggc gatgcgctgc   1320 gaatcggag cggcgatacc gtaaagcacg aggaagcggt cagcccattc gccgccaagc   1380
tcttcagcaa tatcacgggt agccaacgct atgtcctgat agcggtccgc cacacccagc   1440
```

```
cggccacagt cgatgaatcc agaaaagcgg ccattttcca ccatgatatt cggcaagcag    1500
gcatcgccat gggtcacgac gagatcctcg ccgtcgggca tgctcgcctt gagcctggcg    1560
aacagttcgg ctggcgcgag ccctgatgc tcttcgtcca gatcatcctg atcgacaaga    1620
ccggcttcca tccgagtacg tgctcgctcg atgcgatgtt tcgcttggtg gtcgaatggg    1680
caggtagccg gatcaagcgt atgcagccgc cgcattgcat cagccatgat ggatactttc    1740
tcggcaggag caaggtgaga tgacaggaga tcctgccccg gcacttcgcc caatagcagc    1800
cagtcccttc ccgcttcagt gacaacgtcg agcacagctg cgcaaggaac gcccgtcgtg    1860
gccagccacg atagccgcgc tgcctcgtct tgcagttcat tcagggcacc ggacaggtcg    1920
gtcttgacaa aaagaaccgg gcgcccctgc gctgacagcc ggaacacggc ggcatcagag    1980
cagccgattg tctgttgtgc ccagtcatag ccgaatagcc tctccaccca agcggccgga    2040
gaacctgcgt gcaatccatc ttgttcaatc atgcgaaacg atcctcatcc tgtctcttga    2100
tcagatcttg atccctgtca gaccaagttt actcatatat actttagatt gatttaaaac    2160
ttcattttta atttaaaagg atctaggtga agatcctttt tgataatctc atgaccaaaa    2220
tcccttaacg tgagtttttcg ttccactgag cgtcagaccc cgtagaaaag atcaaaggat    2280
cttcttgaga tccttttttt ctgcgcgtaa tctgctgctt gcaaacaaaa aaaccaccgc    2340
taccagcggt ggtttgtttg ccggatcaag agctaccaac tctttttccg aaggtaactg    2400
gcttcagcag agcgcagata ccaaatactg ttcttctagt gtagccgtag ttaggccacc    2460
acttcaagaa ctctgtagca ccgcctacat acctcgctct gctaatcctg ttaccagtgg    2520
ctgctgccag tggcgataag tcgtgtctta ccgggttgga ctcaagacga tagttaccgg    2580
ataaggcgca gcggtcgggc tgaacggggg gttcgtgcac acagcccagc ttggagcgaa    2640
cgacctacac cgaactgaga tacctacagc gtgagctatg agaaagcgcc acgcttcccg    2700
aagggagaaa ggcggacagg tatccggtaa gcggcagggt cggaacagga gagcgcacga    2760
gggagcttcc aggggggaaac gcctggtatc tttatagtcc tgtcgggttt cgccacctct    2820
gacttgagcg tcgattttg tgatgctcgt caggggggcg gagcctatgg aaaaacgcca    2880
gcaacgcgg                                                           2889
```

Specific Models for Carrying Out the Present Invention

The present application will be described with reference to the following examples which are intended to illustrate (not limit the present application) the present application.

Unless otherwise specified, the molecular biology experimental methods and immunoassay methods used in the present application basically refer to J. Sambrook et al., Molecular Cloning: Laboratory Manual, 2nd Edition, Cold Spring Harbor Laboratory Press, 1989, and FM Ausubel et al., Compiled Molecular Biology Experiment Guide, 3rd edition, John Wiley & Sons, Inc., 1995; the restriction enzymes were used in accordance with the conditions recommended by the product manufacturer. Those skilled in the art know that the examples describe the present application by way of example, and are not intended to limit the scope sought to be protected by the present application.

Example 1: Preparation of hHGF and Its Mutants

The amino acid sequence of nature hHGF (SEQ ID NO: 1) could be found in NCBI accession number NP_000592.3. Using SEQ ID NO:1 as a template, the following three hHGF mutants were designed:

(1) hHGF mutant 130Arg-hHGF, that was obtained by mutating Ser at position 130 of SEQ ID NO: 1 to Arg, and its amino acid sequence was shown in SEQ ID NO: 2;
(2) hHGF mutant 130His-hHGF, that was obtained by mutating Ser at position 130 of SEQ ID NO: 1 to His, and its amino acid sequence was shown in SEQ ID NO: 3;
(2) hHGF mutant 130Lys-hHGF, that was obtained by mutating Ser at position 130 of SEQ ID NO: 1 to Lys, and its amino acid sequence was shown in SEQ ID NO: 4.

Full-gene synthesis was performed to obtain the polynucleotides encoding natural hHGF (SEQ ID NO: 1) and the above three hHGF mutants (SEQ ID NO: 2, SEQ ID NO: 3, SEQ ID NO: 4), respectively, restriction enzyme cleavage sites and initiation codons were introduced at their 5' ends, and restriction enzyme cleavage sites and termination codons were introduced at their 3' ends, so as to obtain nucleic acid molecules encoding natural hHGF and various mutants.

The nucleic acid molecules prepared as described above were cloned into expression vectors, and transformed into CHO host cells, respectively. Under conditions that allowed the expression of foreign proteins, the transformed CHO host cells were cultured, and then the cultures were collected and centrifuged to obtain supernatants containing the target proteins (natural hHGF, 130Arg-hHGF, 130His-hHGF, or 130Lys-hHGF). According to the manufacturer's instructions, an anion exchange chromatography medium (DEAE Sepharose Fast Flow, GE healthcare, 17-0709-10) was used to separate the target proteins in the supernatants, and a heparin affinity chromatography medium (Heparin Sepharose 6 Fast Flow, GE healthcare, 17-0998-01) was used to further purify the target proteins.

The purified target proteins were detected by non-reduced polyacrylamide gel electrophoresis (non-reduced SDS-PAGE, Molecular Cloning Experiment Guide, $4^{th}$ Edition), and the results were shown in FIG. 1. As shown in FIG. 1, the obtained four purified target proteins (natural hHGF, 130Arg-hHGF, 130His-hHGF and 130Lys-hHGF) all had a purity of more than 98% and could be used for follow-up researches.

Example 2: Preparation of Recombinant Plasmids Encoding hHGF and Its Mutants

Full-gene synthesis was performed to obtain polynucleotides respectively encoding natural hHGF (SEQ ID NO: 1) and the above three hHGF mutants (SEQ ID NO: 2, SEQ ID NO: 3, SEQ ID NO: 4), which respectively had the nucleotide sequences as shown in SEQ ID NOs: 5-8. The polynucleotide molecules prepared as above were respectively cloned into pSN vector (see, for example, Chinese Patent CN 108611367 B; its nucleotide sequence was shown in SEQ ID NO: 9), and then transformed into E. coli. After screening and sequencing verification, engineered strains containing the target recombinant plasmids were obtained. The constructed engineered strains were subjected to fermentation, and the plasmids were extracted to obtain stock solutions containing the target recombinant plasmids. The target recombinant plasmids were specifically as follows:
  (1) pSN-hHGF, which carried the polynucleotide (SEQ ID NO: 5) encoding natural hHGF (SEQ ID NO: 1);
  (2) pSN-130Arg-hHGF, which carried the polynucleotide (SEQ ID NO: 6) encoding 130Arg-hHGF (SEQ ID NO: 2);
  (3) pSN-130His-hHGF, which carried the polynucleotide (SEQ ID NO: 7) encoding 130His-hHGF (SEQ ID NO: 3); and
  (4) pSN-130Lys-hHGF, which carried the polynucleotide (SEQ ID NO: 8) encoding 130Lys-hHGF (SEQ ID NO: 4).

The contents of plasmids in the prepared stock solutions were determined by using ultraviolet spectrophotometer. The results showed that the contents of plasmids in the various prepared stock solutions were in the range of 2.0 to 2.2 mg/mL. Specifically, the contents of recombinant plasmids in the four stock solutions were: 2.12 mg/mL (pSN-hHGF), 2.05 mg/mL (pSN-130Arg-hHGF), 2.15 mg/mL (pSN-130His-hHGF) and 2.10 mg/mL (pSN-130Lys-hHGF), respectively.

The stock solutions containing the target recombinant plasmids were taken, diluted with water for injection to plasmid concentration of about 30 µg/ml, and then subjected to purity detection by HPLC. The detection conditions used were as follows:

The chromatographic column used was an anion exchange HPLC analytical column DNA-NPR, which was equilibrated with a buffer of 20 mM Tris-HCl, 0.5M NaCl, pH8.8. After equilibration, the samples were loaded and detected. The loading volume was 100 µl, the flow rate was 0.5 ml/min, and the detection wavelength was 260 nm. After loading the samples, the equilibration was performed by using a buffer of 20 mM Tris-HCl, 0.5M NaCl, pH8.8 (5 min), and then linear gradient elution was carried out under the conditions as follows: (1) by linearly transiting from 100% of solution A (the solution A was 20 mM Tris-HCl, 0.5M NaCl, pH8.8) to 100% of solution B (the solution B was 20 mM Tris-HCl, 0.8M NaCl), the elution was performed for 30 min; and (2) then by using a buffer of 20 mM Tris-HCl, 0.8M NaCl, pH8.8, the elution was performed for 5 min. The results showed that in the various samples of the prepared stock solutions, the plasmids all had HPLC purity of greater than 95.0%. Specifically, the HPLC purity values of the recombinant plasmids in the four stock solutions were: 97.5% (pSN-hHGF), 98.2% (pSN-130Arg-hHGF), 98.0% (pSN-130His-hHGF), 97.8% (pSN-130Lys-hHGF), respectively.

Example 3: Evaluation of In Vitro Biological Activity of hHGF Mutants and Natural hHGF In this example, an in vitro endothelial cell migration experiment was used to evaluate the effects of hHGF mutants and natural hHGF on endothelial cell migration, so as to evaluate the in vitro biological activities of hHGF mutants and natural hHGF.

1. MATERIALS AND METHODS 1.1 Protein Samples
  The hHGF mutants prepared as above (130Arg-hHGF, 130His-hHGF and 130Lys-hHGF) and natural hHGF were formulated to have required concentrations with normal saline before use.
1.2 Cell Line
  ECV304 cell line (umbilical vein endothelial cells) was used to test the biological activity of HGF.
1.3 Reagents
  DMEM medium: Provided by Hyclone. The preparation method was as follows: 1 bag of DMEM medium powder (specification was 1 L) was taken, added with water to dissolve and diluted to 1000 ml, and then added with 2.1 g of sodium bicarbonate. Then, the prepared medium was sterilized and filtered, and stored at 4° C.
  Complete medium: 100 ml of fetal bovine serum was taken and added with the DMEM medium to 1000 ml.
  Transwells: Provided by Costar.
1.4 Instruments
  Carbon dioxide cell incubator: Provided by Medical Equipment Factory of Shanghai Boxun Industrial Co., Ltd., model: HH. CP.
  Inverted microscope: Provided by Chongqing Optoelectronic Instrument Corporation, model: XDS-1B.
  Ultra-clean workbench: Provided by Suzhou Purification Equipment Co., Ltd., model: SW-CJ-1F.
  Bench-top cell washing centrifuge: Provided by Hunan Xingke Scientific Instrument Co., Ltd., model TDL-50B.
  Optical microscope: Provided by Chongqing Optoelectronic Instrument Corporation, model: BP104.
1.5 Experimental Method
  According to the method of "in vitro HGF activity detection test" (The chemotactic effect of mixtures of antibody and antigen on polymorphonuclear leucocytes. J. Exp. Med., 1962, 115: 453-466), the cell migration test was performed.

In short, 600 μl of DMEM medium was added into each well of the lower tank of the migration plate so as to submerge the Transwells therein. The ECV304 cells digested with 0.1% trypsin were prepared with 1640 medium containing 10% fetal bovine serum to form a cell suspension containing $1 \times 10^6$ cells per 1 ml. To each well, 200 μl of cell suspension was added and incubated at 37° C. for 1 h. Then, the original DMEM medium in the lower tank of the migration plate was replaced with 600 μl of medium containing 2 μg of natural hHGF or hHGF mutant, and the incubation was continued for 2 hours. After the incubation, the Transwells were transferred to another well with 20% paraformaldehyde, and the cells were fixed for 10 minutes. The non-migrated cells on the membrane were gently wiped off using cotton swab, and then stained with crystal violet for 5 min. The membrane was carefully removed using scalpel blade, placed on a glass slide (the side with cells was up), and observed with an optical microscope. In addition, a blank control that did not use natural hHGF or hHGF mutant is also provided.

In this test, the count of migrating cells was used to evaluate the biological activity of the protein to be tested (natural hHGF or hHGF mutant). The method of quantitatively evaluating cell migration with optical microscope was as follows: firstly, an area with uniform cell distribution was selected under a low-power (4× objective) optical microscope, then a medium-power (20× objective) microscope with grid attached to the eyepiece was used to select randomly and continuously 5 fields of view, and the count of migrating cells was performed. The measurement results were analyzed and evaluated by statistical t test method.

1.6 Statistical Analysis

The data were expressed as mean±standard deviation ($\bar{x} \pm SD$). Using SPSS16.0 statistical software, the variance analysis for multivariate factorial design data was used for statistical analysis.

2. EXPERIMENTAL RESULTS

As described above, in the in vitro test, the effects of hHGF mutants and natural hHGF on endothelial cell migration was evaluated by performing an endothelial cell migration test with hHGF mutants and natural hHGF. The experimental results were shown in Table 1.

TABLE 1

Effects of hHGF mutants and natural hHGF on endothelial cell migration

| Group | Number of times | Number of migrating cells (cells/field of view) |
|---|---|---|
| Blank control group | 3 | 30.7 ± 8.1 |
| Natural hHGF | 3 | 98.1 ± 11.5* |
| 130Arg-hHGF | 3 | 415.7 ± 33.1**,## |
| 130His-hHGF | 3 | 355.3 ± 27.3**,## |
| 130Lys-hHGF | 3 | 388.9 ± 35.6**,## | wherein, *means $p < 0.05$ compared with the blank control group;
**means $p < 0.01$ compared with the blank control group;
# means $p < 0.05$ compared with the natural hHGF test group;
## means $p < 0.01$ compared with the natural hHGF test group.

As shown in Table 1, in the blank control wells, few endothelial cells passed through the migration membrane; while in the test wells containing hHGF mutants or natural hHGF, the number of migrating cells was significantly increased. Compared with the blank control wells, there were significant differences (test wells containing natural hHGF: $p < 0.05$; test wells containing hHGF mutants: $p < 0.01$). Furthermore, in the test wells containing hHGF mutants, the numbers of migrating cells were significantly higher than that of the test wells containing natural hHGF ($p < 0.01$). These results indicated that both hHGF mutants and natural hHGF could induce/stimulate the migration of endothelial cells, and that the hHGF mutants had stronger ability to induce endothelial cell migration as compared with the natural hHGF. The three hHGF mutants (130Arg-hHGF, 130His-hHGF and 130Lys-hHGF) of the present application could better promote the cell migration.

Example 4: Evaluation of Therapeutic Effect of hHGF Mutants and Natural hHGF on Rabbit Lower Extremity Artery Ischemia Model In this example, a rabbit lower extremity artery ischemia model was used to evaluate the effects of hHGF mutants and natural hHGF on the re-formation of blood vessels and collateral circulation in the rabbit lower extremity ischemia model, thereby evaluating the therapeutic effects of hHGF mutants and natural hHGF.

1. MATERIALS AND METHODS 1.1 Protein Samples

The hHGF mutants prepared as above (130Arg-hHGF, 130His-hHGF and 130Lys-hHGF) and natural hHGF were formulated to have required concentrations with normal saline before use.

1.2 Animal Model

New Zealand male white rabbits, 12-14 months old, body weight 3.5 to 4.0 kg, provided by Beijing Weitong Lihua Company. According to the method described by Takeshita et al. (Therapeutics the formation of a blood vessel. A single intraarterial bolus of vascular endothelial growth factor augments revascularization in a rabbit ischemic hind limb model. J. Clin. Invest., 1994, 93: 662-670), the rabbit lower extremity artery ischemia model was established. After intramuscular injection of Xylazine at a dose of 5 mg/kg, the rabbits were anesthetized with Ketamine at a dose of 50 mg/kg. The inner skin of the left thigh was disinfected with alcohol and iodine. Under aseptic conditions, the skin of the thigh from the midpoint of the groin to the knee joint on the left side was cut, the myofascial membrane was cut, the muscles were separated to fully expose the femoral artery, its main trunk and branches were ligated, and the artery from the femoral artery root to the popliteal artery and the artery at the bifurcation of the great saphenous artery were excised. After ensuring that there was no bleeding, the myofascial membrane and skin were sutured. After the operation, continuous intramuscular injection of gentamicin (3 mg/kg/d) was carried out for 3 days to prevent infection, and intramuscular injection of morphine (0.3 mg/kg/d) was carried out for 10 days for analgesia. On the $10^{th}$ day after the operation, an arterial cannula was inserted into the right carotid artery, a 3F catheter (Terumo, Japan) was inserted into the entrance of the left internal iliac artery, 5 ml of contrast agent was infused at a rate of 1 ml per second, and selective internal iliac angiography was performed to confirm the establishment of sick animal model.

1.3 Animal Grouping

On the $10^{th}$ day after the establishment of the animal model, the animals were randomly divided into model control group (6), hHGF test group (8), 130Arg-hHGF test group (8), 130His-hHGF test group (8) and 130Lys-hHGF test group (8).

1.4 Method of Administration

Four points at the ischemic site of the left inner thigh of each animal (1 point for adductor muscle, and 3 points for semimembranosus muscle) were taken, and 250 μg/250 μl test drug was administrated to each point by intramuscular injection (that was, 1 mg/1 ml of the test drug was administrated once per animal), once a day. The model control group was given an equal volume of saline. The administration was continued for 15 days, a total of 15 administrations.

1.5 Evaluation of Effect of Drugs on the Formation of a Blood Vessel by Selective Internal Iliac Angiography Since the collateral circulation of the lower extremity artery ischemia model animals originated from the branches of the internal iliac artery, selective internal iliac angiography was performed on the $10^{th}$ and $40^{th}$ day (the $30^{th}$ day after the first administration) after the operation to observe the formation of collateral circulation before and after the administration. A 3F catheter (Terumo, Japan) was inserted into the right carotid artery, passed through the abdominal aorta, and placed at the left internal iliac artery entrance. A total of 5 ml of contrast agent was injected at a speed of 1 ml/sec, and Cine film photography was performed. On the $4^{th}$ second angiogram, three straight lines perpendicular to the femur and dividing the femur into 4 parts were drawn on the femur, the number of blood vessels crossing the straight lines were counted, the counting was repeated for 3 times, and the average thereof was taken.

1.6 Histological Determination of Capillary Density

On the $40^{th}$ day after the operation, the ischemic muscle tissues of the lower limbs (adductor muscles and semimembranous muscles) were taken, placed into O.C.T. compound (Miles Inc., Elkhart, USA) solution, and quickly frozen with liquid nitrogen, and then the tissues were frozen and sectioned. According to the Indoxyl-tetrazolium method, the capillary endothelial cells were stained with alkaline phosphatase. Under the microscope (×200), the number of capillary endothelial cells in the tissue was counted, which was then convert into the number of capillaries per 1,000 muscle cells so as to quantify the density of capillaries.

1.7 Statistical Analysis

The data were expressed as mean±standard deviation ($\bar{x}\pm SD$). Using SPSS16.0 statistical software, the variance analysis for multi-factor factorial design data was used to perform statistical analysis.

2. EXPERIMENTAL RESULTS

The detection results of the number of collateral vessels at the ischemic site and the number of new collateral vessels at the ischemic site before and after the administration of each group of experimental animals were shown in Table 2.

TABLE 2

Counting results of collateral vessels of each group of animals

| Group | Number of animals | Before administration (number) | Day 30 after administration (number) | Increment (number) |
|---|---|---|---|---|
| Model control group | 6 | 39.87 ± 3.10 | 43.52 ± 2.16 | 3.65 ± 2.25 |
| hHGF | 8 | 38.73 ± 3.22 | 51.39 ± 3.82* | 12.66 ± 2.96** |
| 130Arg-hHGF | 8 | 40.47 ± 2.76 | 62.37 ± 2.27 | 21.90 ± 2.47**\*### |
| 130His-hHGF | 8 | 42.29 ± 1.87 | 60.73 ± 3.25 | 18.44 ± 2.48**\*# |
| 130Lys-hHGF | 8 | 45.07 ± 3.61 | 64.35 ± 1.97 | 19.28 ± 2.65**\*### | wherein, *means $p < 0.05$ compared with the model control group;
**means $p < 0.01$ compared with the model control group;
means $p < 0.05$ compared with the hHGF test group;
means $p < 0.01$ compared with the hHGF test group.

As shown in Table 2, there was no significant difference (between the five groups) in the number of collateral vessels of experimental animals in each group before administration ($p>0.05$). After administration, the number of collateral vessels in the model control group was not statistically different from that before administration ($p>0.05$); while the numbers of collateral vessels in the four test groups were significantly increased than before administration. When comparing between the groups, the increments of vessels of the three hHGF mutant test groups were all significantly greater than that of the hHGF test group ($p<0.05$).

The experimental results in Table 2 showed that the three hHGF mutants and natural hHGF had good therapeutic effects on lower extremity artery ischemia. Compared with the model control group, each test group could significantly promote the formation of collateral vessels, as shown by angiography. On the $30^{th}$ day after treatment (calculated from the first day of administration), the density of arterioles in the left hind limb of the rabbits of experimental group was significantly higher than that of the model control group. Furthermore, the treatment results of the three hHGF mutants were significantly different from that of the natural hHGF test group: the densities of left hind limb arterioles of the rabbits receiving the hHGF mutants were higher than that of the rabbits receiving the natural hHGF; in which the 130Arg-hHGF test group ($p<0.01$), 130His-hHGF test group ($p<0.05$) and 130Lys-hHGF test group ($p<0.01$) were significantly better than the natural hHGF test group in promoting the formation of collateral vessels. These results indicated that the three hHGF mutants of the present application were unexpectedly superior to natural hHGF in the treatment of lower extremity artery ischemia.

Example 5: Evaluation of Therapeutic Effect of Recombinant Plasmids Encoding hHGF or Its Mutants on Rabbit Lower Extremity Artery Ischemia Model In this example, a rabbit lower extremity artery ischemia model was used to evaluate the effects of recombinant plasmids encoding hHGF or its mutants in promoting the formation of collateral vessels, so as to evaluate the therapeutic effects of recombinant plasmids encoding hHGF or its mutants.

1. MATERIALS AND METHODS

1.1 Plasmid Samples

The four recombinant plasmids prepared as above (pSN-hHGF, pSN-130Arg-hHGF, pSN-130His-hHGF and pSN-130Lys-hHGF) were formulated to have the required concentration with physiological saline before use.

1.2 Animal Model

New Zealand male white rabbits, 12-14 months old, body weight 3.5 to 4.0 kg, provided by Beijing Weitong Lihua Company. According to the method described by Takeshita et al. (Therapeutics the formation of a blood vessel. A single intraarterial bolus of vascular endothelial growth factor augments revascularization in a rabbit ischemic hind limb model. J. Clin. Invest., 1994, 93: 662-670), the rabbit lower extremity artery ischemia model was established. After intramuscular injection of Xylazine at a dose of 5 mg/kg, the rabbits were anesthetized with Ketamine at a dose of 50 mg/kg. The inner skin of the left thigh was disinfected with alcohol and iodine. Under aseptic conditions, the skin of the thigh from the midpoint of the groin to the knee joint on the left side was cut, the myofascial membrane was cut, the muscles were separated to fully expose the femoral artery, its main trunk and branches were ligated, and the artery from the femoral artery root to the popliteal artery and the artery at the bifurcation of the great saphenous artery were excised. After ensuring that there was no bleeding, the myofascial membrane and skin were sutured. After the operation, continuous intramuscular injection of gentamicin (3 mg/kg/d) was carried out for 3 days to prevent infection, and intramuscular injection of morphine (0.3 mg/kg/d) was carried out for 10 days for analgesia. On the $10^{th}$ day after the operation, an arterial cannula was inserted into the right carotid artery, a 3F catheter (Terumo, Japan) was inserted into the entrance of the left internal iliac artery, 5 ml of contrast agent was infused at a rate of 1 ml per second, and selective internal iliac angiography was performed to confirm the establishment of sick animal model.

1.3 Animal Grouping

On the $10^{th}$ day after the establishment of the animal model, the animals were randomly divided into model control group (8), pSN-hHGF test group (8), pSN-130Arg-hHGF test group (8), pSN-130His-hHGF test group (8) and pSN-130Lys-hHGF test group (8).

1.4 Method of Administration

Four points at the ischemic site of the left inner thigh of each animal (1 point for adductor muscle, and 3 points for semimembranosus muscle) were taken, and 250 µg/250 µl test drug was administrated to each point by intramuscular injection (that was, 1 mg/1 ml of the test drug was administrated once per animal) for a total of 1 administration. The model control group was given an equal volume of saline.

1.5 Evaluation of Effect of Drugs on the Formation of a Blood Vessel by Selective Internal Iliac Angiography Since the collateral circulation of the lower extremity artery ischemia model animals originated from the branches of the internal iliac artery, selective internal iliac angiography was performed on the $10^{th}$ and $40^{th}$ day (the $30^{th}$ day after the first administration) after the operation to observe the formation of collateral circulation before and after the administration. A 3F catheter (Terumo, Japan) was inserted into the right carotid artery, passed through the abdominal aorta, and placed at the left internal iliac artery entrance. A total of 5 ml of contrast agent was injected at a speed of 1 ml/sec, and Cine film photography was performed. On the $4^{th}$ second angiogram, three straight lines perpendicular to the femur and dividing the femur into 4 parts were drawn on the femur, the number of blood vessels crossing the straight lines were counted, the counting was repeated for 3 times, and the average thereof was taken.

1.6 Statistical Analysis

The data were expressed as mean±standard deviation ($\bar{x}$±SD). Using SPSS16.0 statistical software, the variance analysis for multi-factor factorial design data was used to perform statistical analysis.

2. EXPERIMENTAL RESULTS

The detection results of the number of collateral vessels at the ischemic site and the number of new collateral vessels at the ischemic site before and after the administration of each group of experimental animals were shown in Table 3.

TABLE 3

Counting results of collateral vessels of each group of animals

| Group | Number of animals | Before administration (number) | Day 30 after administration (number) | Increment (number) |
|---|---|---|---|---|
| Model control group | 8 | 45.62 ± 2.15 | 48.92 ± 3.75 | 3.30 ± 2.82 |
| pSN-hHGF | 8 | 42.51 ± 4.30 | 55.78 ± 4.57* | 13.27 ± 4.32* |
| pSN-130Arg-hHGF | 8 | 46.73 ± 5.22 | 78.37 ± 3.32* | 31.64 ± 4.80**## |
| pSN-130His-hHGF | 8 | 48.32 ± 2.84 | 80.54 ± 6.28* | 32.22 ± 4.91**## |
| pSN-130Lys-hHGF | 8 | 46.72 ± 5.14 | 78.41 ± 4.20* | 31.69 ± 4.18**## | wherein, *means $p < 0.05$ compared with the model control group;
**means $p < 0.01$ compared with the model control group;
"#" means $p < 0.05$ compared with the pSN-hHGF test group;
means $p < 0.01$ compared with the pSN-hHGF test group.

As shown in Table 3, there was no significant difference (between the five groups) in the number of collateral vessels of experimental animals in each group before the administration ($p>0.05$). After administration, the number of collateral vessels in the model control group was not statistically different from that before administration ($p>0.05$); while the numbers of collateral vessels in the four test groups were significantly increased than before administration. When comparing between the groups, the increments of vessels of the 3 test groups of recombinant plasmids encoding hHGF mutants (pSN-130Arg-hHGF, pSN-130His-hHGF and pSN-130Lys-hHGF) were all significantly greater than that of the test group of recombinant plasmid encoding natural hHGF (pSN-hHGF) ($p<0.01$).

The experimental results in Table 3 showed that the recombinant plasmids encoding hHGF or its mutants all had good therapeutic effects on lower extremity artery ischemia. Compared with the model control group, each test group could significantly promote the formation of collateral vessels. Furthermore, the experimental results in Table 3 also showed that the therapeutic results of the three recombinant plasmids encoding hHGF mutants were significantly different from that of the recombinant plasmid encoding natural hHGF, that was, the pSN-130Arg-hHGF test group ($p<0.01$), pSN-130His-hHGF test group ($p<0.01$) and pSN-130Lys-hHGF test group ($p<0.01$) were all significantly better than the pSN-hHGF test group in promoting collateral vessel formation. These results indicated that the three recombinant plasmids encoding hHGF mutants (pSN-130Arg-hHGF, pSN-130His-hHGF, and pSN-130Lys-hHGF) were unexpectedly superior to the recombinant plasmid encoding natural hHGF (pSN-hHGF) in aspect of treatment effect on lower extremity artery ischemia.

Example 6: Evaluation of Therapeutic Effect of hHGF Mutants and Natural hHGF on Rat Diabetic Peripheral Neuropathy Model In this example, a rat diabetic peripheral neuropathy model was used to evaluate the effects of hHGF mutants and natural hHGF in the treatment of diabetic peripheral neuropathy.

1. MATERIALS AND METHODS

1.1 Protein Samples

The hHGF mutants prepared as above (130Arg-hHGF, 130His-hHGF and 130Lys-hHGF) and natural hHGF were formulated to have the required concentration with normal saline before use.

1.2 Instruments

ONE-TOUCH Select Simple blood glucose meter: Provided by Johnson & Johnson;
Neuromatic-2000 electromyography instrument: Provided by Dandi;
EG1160 paraffin embedding machine: Provided by Leica, Germany;
RM2255 slicer: Provided by Leica, Germany;
DM6000B optical microscope: Provided by Leica, Germany.

1.3 Animal Model

Wistar rats (SPF grade, male, body weight 180-200 g, 2.5 to 3 months old) were provided by Beijing Weitong Lihua Company. After the rats were bought back, they were fed adaptively for 5 days, and the animals were confirmed to be in good condition. 10 rats were randomly selected as the normal control group, and the remaining 60 rats were modeled as follows. The rats were fasted for 12 hours without fasting water, and then weighed, measured to determine blood glucose, and numbered. Streptozotocin (STZ) was added into the pre-prepared 0.1 mol/L citric acid/sodium citrate buffer (pH 4.4) under ice bath environment to prepare 2% STZ solution. The STZ was administered once to the modeled animals by intraperitoneal injection on the left side at a dose of 65 mg/kg; the animals in the normal control group received the same dose of the same buffer by left intraperitoneal injection. After 72 hours, the blood glucose values of the rats were measured. A total of 52 rats with blood glucose >16.7 mmol/L and urine glucose from +++ to ++++ were selected as model animals. After 10 weeks of feeding, the model rats with diabetic peripheral neuropathy were obtained.

1.4 Animal Grouping

The 52 model rats were randomly divided into model control group (10), hHGF test group (10), 130Arg-hHGF test group (10), 130His-hHGF test group (11), 130Lys-hHGF test group (11 only).

1.5 Method of Administration

The animals in the test groups began to receive the drugs after 10 weeks of successful modeling. Four points on the left inner thigh of each animal (1 point for adductor muscle and 3 points for semimembranous muscle) were taken, and 250 μg/250 μl test drug was administrated to each point by intramuscular injection (that was, a total of 1 mg/1 ml test drug was administrated to each animal once), 1 administration per day. The model group was given an equal volume of normal saline for 20 days for a total of 20 injections.

1.6 Measurement of Motor Nerve Conduction Velocity (MNCV) and Sensory Nerve Conduction Velocity (SNCV)

The measurement was performed at the $10^{th}$ week after the first administration. After the rats were anesthetized, the left sciatic nerve was surgically separated, and the MNCV and SNCV of the rats were measured with Neuromatic-2000 electromyography instrument. The MNCV measurement method was as follows: the recording electrode was vertically pierced into the middle of the abdominal part of the tibialis anterior muscle, the stimulating electrode was used to stimulate the proximal end of the sciatic nerve with a stimulation current of 20 mA, the electromyography instrument displayed and recorded the action potential on the oscilloscope, and then the MNCV was calculated according to the distance between the two electrodes. The SNCV measurement method was as follows: the recording electrode was placed at the proximal end of the sciatic nerve, the stimulating electrode was used to stimulate the proximal end of the sural nerve with a stimulation current of 30 mA, the electromyography instrument recorded the obtained waveform, and then the SNCV was calculated according to the distance between the two electrodes.

1.7 Quantitative Analysis of Myelinated Nerve Fibers of Sural Nerve

The measurement was performed at the $10^{th}$ week after the first administration. The distal end of the right sural nerve was fixed in 3% glutaraldehyde/0.1 mol/L phosphate buffer and kept at 4° C. overnight; rinsed with PBS buffer, fixed with 1% osmium acid, then rinsed, dehydrated, and embedded with epoxy resin. 1 μm semi-thin cross-sectional sections were prepared, stained with 1% toluidine blue solution for 30 minutes, then washed with 85% alcohol, decolorized until the background was light blue, and then the slide was mounted with gum. The images of cross sections of sural nerve were collected at 200 times magnification, the myelinated nerve fibers were counted by using a multifunctional true color pathological image analysis system, the total cross-sectional area of sural nerve fibers, the nerve fiber density and the average cross-sectional area of nerve fibers were measured so as to observe the pathological changes of the sural nerve.

1.8 Statistical Processing

The data were expressed as mean±standard deviation ($\bar{x}\pm SD$). Using SPS S16.0 statistical software, the variance analysis for multi-factor factorial design data was used to perform statistical analysis.

2. EXPERIMENTAL RESULTS

2.1 Determination of MNCV and SNCV of Experimental Animals in Each Group

Table 4 showed the measurement results of MNCV and SNCV of experimental animals in each group.

TABLE 4

MNCV and SNCV of animals in each group at the $10^{th}$ week after the first administration

| Group | MNCV | SNCV |
| --- | --- | --- |
| Normal control group | 43.5 ± 4.7 | 46.7 ± 5.3 |
| Model control group | 31.6 ± 3.5** | 33.2 ± 5.7** |
| hHGF group | 35.2 ± 3.2* | 38.9 ± 4.5* |
| 130Arg-hHGF group | 42.8 ± 4.7 | 44.8 ± 5.6 |
| 130His-hHGF group | 40.3 ± 4.3 | 39.7 ± 3.8 |
| 130Lys-hHGF group | 39.5 ± 3.8 | 42.6 ± 4.5 | wherein, *means $p < 0.05$ compared with the normal control group;
**means $p < 0.01$ compared with the normal control group.

As shown in Table 4, at the $10^{th}$ week after the first administration, the MNCV and SNCV of the model control group were the lowest (significantly slower than those of the normal control group, $p<0.01$); the hHGF test group followed (significantly slower than those of the normal control group, $p<0.05$). The MNCV and SNCV of the hHGF mutant groups were slightly lower than those of the normal control group, but the difference was not statistically significant ($p>0.05$). These results indicated that natural hHGF and hHGF mutants could promote the repair of diabetic peripheral neuropathy, restore the damaged MNCV and SNCV, and that the therapeutic effects of hHGF mutants were better than that of natural hHGF.

2.2 Quantitative Analysis of Myelinated Nerve Fibers of Sural Nerve

The results of quantitative analysis of the myelinated nerve fibers of sural nerve of experimental animals in each group were shown in Table 5.

TABLE 5

Quantitative analysis of myelinated nerve fibers of sural nerve in each group of animals at the 10th week after the first administration

| Group | Total nerve cross-sectional area ($\mu m^2$) | Average nerve fiber area ($\mu m^2$) |
| --- | --- | --- |
| Normal control group | 31771 ± 1265 | 23.5 ± 2.1 |
| Model control group | 16449 ± 1082** | 13.7 ± 1.4** |
| hHGF group | 20454 ± 1571* | 17.3 ± 2.5* |
| 130Arg-hHGF group | 27539 ± 1852[#] | 22.9 ± 1.7[#] |
| 130His-hHGF group | 25991 ± 1451[#] | 20.3 ± 1.1[#] |
| 130Lys-hHGF group | 26193 ± 1615[#] | 19.9 ± 2.1[#] | wherein, *means $p < 0.05$ compared with the normal control group;
**means $p < 0.01$ compared with the normal control group.
[#]means $p < 0.05$ compared with the hHGF test group;
"##" means $p < 0.01$ compared with the hHGF test group.

As shown in Table 5, at the 10th week after the first administration, compared with the normal control group, the total nerve cross-sectional area and the average nerve fiber area of the model control group were significantly reduced, and there was a significant difference ($p<0.01$); the total nerve cross-sectional area and average nerve fiber area of the animals in the hHGF test group also decreased significantly ($p<0.05$), but the degree of reduction decreased; the total nerve cross-sectional area and average nerve fiber area of the animals in the hHGF mutant test groups showed non-obvious reduction, and there was no significant difference. Furthermore, compared with the hHGF test group, the total nerve cross-sectional area and the average nerve fiber area of the hHGF mutant test groups were significantly increased ($p<0.05$). These results indicated that the natural hHGF and hHGF mutants could promote the repair of diabetic peripheral neuropathy, restore the total cross-sectional area of myelinated nerve fibers and the average area of nerve fibers of the sural nerve, and that the therapeutic effects of hHGF mutants were better than that of natural hHGF.

The results in Table 4-5 showed that both hHGF mutants and natural hHGF had a good therapeutic effects on diabetic peripheral neuropathy, could significantly increase MNCV and SNCV in diabetic rats, and significantly improve the total cross-sectional area of sural nerve fibers in diabetic rats and the average area of nerve fibers. In addition, the treatment results of the three hHGF mutants were significantly better than those of the natural hHGF. The three hHGF mutants of the present application were unexpectedly superior to the natural hHGF in the treatment of diabetic peripheral neuropathy in rats.

Example 7: Evaluation of Therapeutic Effects Recombinant Plasmids Encoding hHGF or Its Mutants on Rat Diabetic Peripheral Neuropathy Model In this example, a rat diabetic peripheral neuropathy model was used to evaluate the effects of recombinant plasmids encoding hHGF or its mutants on diabetic peripheral neuropathy.

1. MATERIALS AND METHODS 1.1 Plasmid Samples

The four recombinant plasmids prepared as above (pSN-hHGF, pSN-130Arg-hHGF, pSN-130His-hHGF and pSN-130Lys-hHGF) were formulated to have the required concentration with physiological saline before use.

1.2 Instruments

ONE-TOUCH Select Simple blood glucose meter: Provided by Johnson & Johnson;

Neuromatic-2000 electromyography instrument: Provided by Dandi;

EG1160 paraffin embedding machine: Provided by Leica, Germany;

RM2255 slicer: Provided by Leica, Germany;

DM6000B optical microscope: Provided by Leica, Germany.

1.3 Animal Model

Wistar rats (SPF grade, male, body weight 180-200 g, 2.5 to 3 months old) were provided by Beijing Weitong Lihua Company. After the rats were bought back, they were fed adaptively for 5 days, and the animals were confirmed to be in good condition. 10 rats were randomly selected as the normal control group, and the remaining 60 rats were modeled as follows. The rats were fasted for 12 hours without fasting water, and then weighed, measured to determine blood glucose, and numbered. Streptozotocin (STZ) was added into the pre-prepared 0.1 mol/L citric acid/sodium citrate buffer (pH 4.4) under ice bath environment to prepare 2% STZ solution. The STZ was administrated once to the modeled animals by intraperitoneal injection on the left side at a dose of 65 mg/kg; the animals in the normal control group received the same dose of the same buffer by left intraperitoneal injection. After 72 hours, the blood glucose values of the rats were measured. A total of 52 rats with blood glucose >16.7 mmol/L and urine glucose from +++ to ++++ were selected as model animals. After 10 weeks of feeding, the model rats with diabetic peripheral neuropathy were obtained.

1.4 Animal Grouping 52 model rats were randomly divided into model control group (10), pSN-hHGF test group (10), pSN-130Arg-hHGF test group (10), pSN-130His-hHGF test group (11), and PSN-130Lys-hHGF test group (11 animals).

1.5 Method of Administration

The animals in the test groups began to receive the drugs after 10 weeks of successful modeling. Four points on the left inner thigh of each animal (1 point for adductor muscle and 3 points for semimembranous muscle) were taken, and 250 μg/250 μl test drug was administrated to each point by intramuscular injection (that was, a total of 1 mg/1 ml test drug was administrated to each animal once), in total of 1 administration. The model group was given an equal volume of normal saline.

1.6 Measurement of Motor Nerve Conduction Velocity (MNCV) and Sensory Nerve Conduction Velocity (SNCV)

The measurement was performed at the 10th week after the administration. After the rats were anesthetized, the left sciatic nerve was surgically separated, and the MNCV and SNCV of the rats were measured with Neuromatic-2000 electromyography instrument. The MNCV measurement method was as follows: the recording electrode was vertically pierced into the middle of the abdominal part of the tibialis anterior muscle, the stimulating electrode was used to stimulate the proximal end of the sciatic nerve with a stimulation current of 20 mA, the electromyography instrument displayed and recorded the action potential on the oscilloscope, and then the MNCV was calculated according to the distance between the two electrodes. The SNCV measurement method was as follows: the recording electrode was placed at the proximal end of the sciatic nerve, the stimulating electrode was used to stimulate the proximal end of the sural nerve with a stimulation current of 30 mA, the electromyography instrument recorded the obtained waveform, and then the SNCV was calculated according to the distance between the two electrodes.

1.7 Quantitative Analysis of Myelinated Nerve Fibers of Sural Nerve

The measurement was performed at the $10^{th}$ week after the administration. The distal end of the right sural nerve was fixed in 3% glutaraldehyde/0.1 mol/L phosphate buffer and kept at 4° C. overnight; rinsed with PBS buffer, fixed with 1% osmium acid, then rinsed, dehydrated, and embedded with epoxy resin. 1 μm semi-thin cross-sectional sections were prepared, stained with 1% toluidine blue solution for 30 minutes, then washed with 85% alcohol, decolorized until the background was light blue, and then the slide was mounted with gum. The images of cross sections of sural nerve were collected at 200 times magnification, the myelinated nerve fibers were counted by using a multifunctional true color pathological image analysis system, the total cross-sectional area of sural nerve fibers, the nerve fiber density and the average cross-sectional area of nerve fibers were measured so as to observe the pathological changes of the sural nerve.

1.8 Statistical Processing

The data were expressed as mean±standard deviation ($\bar{x}\pm SD$). Using SPSS16.0 statistical software, the variance analysis for multi-factor factorial design data was used to perform statistical analysis.

2. EXPERIMENTAL RESULTS 2.1 Determination of MNCV and SNCV of Experimental Animals in Each Group Table 6 showed the measurement results of MNCV and SNCV of experimental animals in each group.

TABLE 6

MNCV and SNCV of animals in each group at the $10^{th}$ week after administration

| Group | MNCV | SNCV |
| --- | --- | --- |
| Normal control group | 51.2 ± 3.6 | 48.5 ± 4.8 |
| Model control group | 33.6 ± 3.0** | 31.5 ± 3.7** |
| pSN-hHGF test group | 36.2 ± 2.8* | 37.6 ± 3.1* |
| pSN-130Arg-hHGF test group | 45.4 ± 4.6 | 48.3 ± 5.1 |
| pSN-130His-hHGF test group | 48.8 ± 4.0 | 47.9 ± 3.1 |
| pSN-130Lys-hHGF test group | 47.5 ± 4.6 | 46.3 ± 3.5 | wherein, *means p < 0.05 compared with the normal control group;
**means p < 0.01 compared with the normal control group.

As shown in Table 6, at the $10^{th}$ week after administration, the MNCV and SNCV of the model control group were the lowest (significantly slower than those of the normal control group, p<0.01); the pSN-hHGF test group followed (significantly slower than those of the normal control group, p<0.05). The MNCV and SNCV of the test groups of recombinant plasmids encoding hHGF mutants were slightly lower than those of the normal control group, but the difference was not statistically significant (p>0.05). These results indicated that the recombinant plasmids encoding natural hHGF and its mutants could promote the repair of diabetic peripheral neuropathy, restore damaged MNCV and SNCV, and the therapeutic effects of the recombinant plasmids encoding hHGF mutants (pSN-130Arg-hHGF, pSN-130His-hHGF and pSN-130Lys-hHGF) were better than those of the recombinant plasmid encoding natural hHGF (pSN-hHGF).

(2) Quantitative Analysis of Myelinated Nerve Fibers of Sural Nerve

The results of quantitative analysis of the myelinated nerve fibers of sural nerve of experimental animals in each group were shown in Table 7.

TABLE 7

Quantitative analysis of myelinated nerve fibers of sural nerve of animals in each group at the $10^{th}$ week after administration

| Group | Total nerve cross-sectional area (μm²) | Average nerve fiber area (μm²) |
| --- | --- | --- |
| Normal control group | 36054 ± 2122 | 25.7 ± 2.0 |
| Model control group | 15398 ± 971** | 10.6 ± 1.2** |
| pSN-hHGF test group | 18123 ± 1025* | 15.2 ± 1.8* |
| pSN-130Arg-hHGF test group | 31352 ± 1659# | 23.9 ± 1.4# |
| pSN-130His-hHGF test group | 28232 ± 1321# | 21.5 ± 0.9# |
| pSN-130Lys-hHGF test group | 29269 ± 1217# | 24.1 ± 1.2# | wherein, *means p < 0.05 compared with the normal control group;
**means p < 0.01 compared with the normal control group.
means p < 0.05 compared with the pSN-hHGF test group;
"##" means p < 0.01 compared with the pSN-hHGF test group.

As shown in Table 7, at the $10^{th}$ week after administration, compared with the normal control group, the total nerve cross-sectional area and the average nerve fiber area of the model control group were significantly reduced, and there was a significant difference (p<0.01); the total nerve cross-sectional area and the average nerve fiber area of the animals in the pSN-hHGF test group were also significantly reduced (p<0.05), but the degree of reduction decreased; the total nerve cross-sectional area and the average nerve fiber area of the animals in the test groups of recombinant plasmids encoding hHGF mutants showed non-obvious reduction, and there was no significant difference. Furthermore, compared with the pSN-hHGF test group, the total nerve cross-sectional area and the average nerve fiber area of the animals in the test groups of recombinant plasmids encoding hHGF mutants were significantly increased (p<0.05). These results indicated that the recombinant plasmids encoding natural hHGF and its mutants could promote the repair of diabetic peripheral neuropathy, restore the total cross-sectional area of myelinated nerve fibers and the average area of nerve fibers of sural nerve, and the therapeutic effects of the three recombinant plasmids encoding hHGF mutants (PSN-130Arg-hHGF, pSN-130His-hHGF and pSN-130Lys-hHGF) were better than those of the recombinant plasmid encoding natural hHGF (pSN-hHGF).

The results in Table 6-7 showed that the recombinant plasmids encoding hHGF mutants and the recombinant plasmid encoding natural hHGF had good therapeutic effects on diabetic peripheral neuropathy, could significantly increase MNCV and SNCV in diabetic rats, and significantly improve the total cross-sectional area of sural nerve fibers and the average area of nerve fibers in diabetic rats. In addition, the treatment results of the three recombinant plasmids encoding hHGF mutants (pSN-130Arg-hHGF, pSN-130His-hHGF and pSN-130Lys-hHGF) were significantly better than those of the recombinant plasmid encoding natural hHGF (pSN-hHGF).

3. CONCLUSION

The results of Examples 3, 4 and 6 showed that the hHGF mutants of the present application had significantly higher activity than natural hHGF in terms of promoting the migration of umbilical vein endothelial cells, promoting the growth of lower extremity arterioles, and promoting the repair of diabetic peripheral neuropathy.

The results of Examples 5 and 7 showed that the recombinant plasmids encoding the hHGF mutants could be used as gene therapy drugs to promote the growth of lower extremity arterioles and promote the repair of diabetic peripheral neuropathy in the subjects, and their therapeutic effects were significantly higher than those of the recombinant plasmid encoding natural hHGF.

Although the specific embodiments of the present application have been described in detail, those skilled in the art will understand that various modifications and changes can be made to the details according to all the teachings that have been disclosed, and these changes are within the scope of protection of the present application. The full scope of the present application is given by the appended claims and any equivalents thereof.

What is claimed is:

1. A mutant of human hepatocyte growth factor (hHGF) comprising the amino acid sequence that is identical to SEQ ID NO: 1 except that the amino acid at 130$^{th}$ position of SEQ ID NO: 1 is substituted with an amino acid selected from the group consisting of arginine, histidine, and lysine.

2. The mutant according to claim 1, wherein the mutant has one or more characteristics selected from the group consisting of:
   (1) the mutant consists of the amino acid sequence selected from the group consisting of SEQ ID NOs: 2, 3 and 4;
   (2) the mutant is prepared by recombinant expression or chemical synthesis; and
   (3) the mutant is modified by PEGylation.

3. A pharmaceutical composition comprising the mutant according to claim 1 and a pharmaceutically acceptable carrier and/or excipient.

4. A method for treating a disease that benefits from an activity of natural hHGF in a subject in need thereof, wherein the method comprises administering to the subject a therapeutically effective amount of the mutant according to claim 1 or a pharmaceutical composition comprising the mutant; and wherein the disease is selected from the group consisting of metabolic syndrome, diabetes, restenosis, coronary artery disease (CAD), peripheral artery disease (PAD), traumatic nerve injury, peripheral neuropathy myocardial infarction, lower extremity artery ischemia, amyotrophic lateral sclerosis (ALS), Parkinson's disease, dementia, and diabetic peripheral neuropathy.

5. The method according to claim 4, wherein the subject is a mammal.

6. The method according to claim 4, wherein the subject is a human.

7. A method for promoting growth and/or migration of an endothelial cell, wherein the method comprises contacting the endothelial cell or administering to a subject in need thereof an effective amount of the mutant according to claim 1 or a pharmaceutical composition comprising the mutant.

8. The method according to claim 7, wherein the endothelial cell is an umbilical vein endothelial cell.

9. A method for promoting formation of a blood vessel in a subject in need thereof, wherein the method comprises administering to the subject an effective amount of the mutant according to claim 1.

10. The method according to claim 9, wherein the blood vessel is a microvessel.

\* \* \* \* \*

UNITED STATES PATENT AND TRADEMARK OFFICE
CERTIFICATE OF CORRECTION

| | |
|---|---|
| PATENT NO. | : 12,264,186 B2 |
| APPLICATION NO. | : 17/420865 |
| DATED | : April 1, 2025 |
| INVENTOR(S) | : Liya Nie et al. |

It is certified that error appears in the above-identified patent and that said Letters Patent is hereby corrected as shown below:

In the Claims

<u>Column 67, Claim 1, Line 55:</u>
"except that the amino acid"
Should read:
-- except the amino acid --.

<u>Column 68, Claim 4, Lines 62-63:</u>
"peripheral neuropathy myocardial"
Should read:
-- peripheral neuropathy, myocardial --.

<u>Column 69, Claim 9, Line 13:</u>
"according to claim 1."
Should read:
-- according to claim 1 or a pharmaceutical composition comprising the mutant. --.

Signed and Sealed this
Third Day of June, 2025

Coke Morgan Stewart
*Acting Director of the United States Patent and Trademark Office*

SEQUENCE LISTING

<160> NUMBER OF SEQ ID NOS: 9

<210> SEQ ID NO 1
<211> LENGTH: 697
<212> TYPE: PRT
<213> ORGANISM: Homo sapiens

<400> SEQUENCE: 1

```
Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
    130                 135                 140

Tyr Cys Arg Asn Pro Arg Gly Glu Glu Gly Gly Pro Trp Cys Phe Thr
145                 150                 155                 160

Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
            180                 185                 190

Asp His Thr Glu Ser Gly Lys Ile Cys Gln Arg Trp Asp His Gln Thr
        195                 200                 205

Pro His Arg His Lys Phe Leu Pro Glu Arg Tyr Pro Asp Lys Gly Phe
    210                 215                 220

Asp Asp Asn Tyr Cys Arg Asn Pro Asp Gly Gln Pro Arg Pro Trp Cys
225                 230                 235                 240

Tyr Thr Leu Asp Pro His Thr Arg Trp Glu Tyr Cys Ala Ile Lys Thr
                245                 250                 255

Cys Ala Asp Asn Thr Met Asn Asp Thr Asp Val Pro Leu Glu Thr Thr
            260                 265                 270

Glu Cys Ile Gln Gly Gln Gly Glu Gly Tyr Arg Gly Thr Val Asn Thr
        275                 280                 285

Ile Trp Asn Gly Ile Pro Cys Gln Arg Trp Asp Ser Gln Tyr Pro His
    290                 295                 300
```

```
Glu His Asp Met Thr Pro Glu Asn Phe Lys Cys Lys Asp Leu Arg Glu
305                 310                 315                 320

Asn Tyr Cys Arg Asn Pro Asp Gly Ser Glu Ser Pro Trp Cys Phe Thr
            325                 330                 335

Thr Asp Pro Asn Ile Arg Val Gly Tyr Cys Ser Gln Ile Pro Asn Cys
        340                 345                 350

Asp Met Ser His Gly Gln Asp Cys Tyr Arg Gly Asn Gly Lys Asn Tyr
            355                 360                 365

Met Gly Asn Leu Ser Gln Thr Arg Ser Gly Leu Thr Cys Ser Met Trp
370                 375                 380

Asp Lys Asn Met Glu Asp Leu His Arg His Ile Phe Trp Glu Pro Asp
385                 390                 395                 400

Ala Ser Lys Leu Asn Glu Asn Tyr Cys Arg Asn Pro Asp Asp Asp Ala
            405                 410                 415

His Gly Pro Trp Cys Tyr Thr Gly Asn Pro Leu Ile Pro Trp Asp Tyr
        420                 425                 430

Cys Pro Ile Ser Arg Cys Glu Gly Asp Thr Thr Pro Thr Ile Val Asn
            435                 440                 445

Leu Asp His Pro Val Ile Ser Cys Ala Lys Thr Lys Gln Leu Arg Val
450                 455                 460

Val Asn Gly Ile Pro Thr Arg Thr Asn Ile Gly Trp Met Val Ser Leu
465                 470                 475                 480

Arg Tyr Arg Asn Lys His Ile Cys Gly Gly Ser Leu Ile Lys Glu Ser
            485                 490                 495

Trp Val Leu Thr Ala Arg Gln Cys Phe Pro Ser Arg Asp Leu Lys Asp
            500                 505                 510

Tyr Glu Ala Trp Leu Gly Ile His Asp Val His Gly Arg Gly Asp Glu
        515                 520                 525

Lys Cys Lys Gln Val Leu Asn Val Ser Gln Leu Val Tyr Gly Pro Glu
    530                 535                 540

Gly Ser Asp Leu Val Leu Met Lys Leu Ala Arg Pro Ala Val Leu Asp
545                 550                 555                 560

Asp Phe Val Ser Thr Ile Asp Leu Pro Asn Tyr Gly Cys Thr Ile Pro
                565                 570                 575

Glu Lys Thr Ser Cys Ser Val Tyr Gly Trp Gly Tyr Thr Gly Leu Ile
            580                 585                 590

Asn Tyr Asp Gly Leu Leu Arg Val Ala His Leu Tyr Ile Met Gly Asn
        595                 600                 605

Glu Lys Cys Ser Gln His His Arg Gly Lys Val Thr Leu Asn Glu Ser
    610                 615                 620

Glu Ile Cys Ala Gly Ala Glu Lys Ile Gly Ser Gly Pro Cys Glu Gly
625                 630                 635                 640

Asp Tyr Gly Gly Pro Leu Val Cys Glu Gln His Lys Met Arg Met Val
                645                 650                 655

Leu Gly Val Ile Val Pro Gly Arg Gly Cys Ala Ile Pro Asn Arg Pro
            660                 665                 670

Gly Ile Phe Val Arg Val Ala Tyr Tyr Ala Lys Trp Ile His Lys Ile
        675                 680                 685

Ile Leu Thr Tyr Lys Val Pro Gln Ser
690                 695

<210> SEQ ID NO 2
<211> LENGTH: 697
```

```
<212> TYPE: PRT
<213> ORGANISM: artificial
<220> FEATURE:
<223> OTHER INFORMATION: amino acid sequence of 130Arg-hHGF

<400> SEQUENCE: 2
```

| | | | | | | | | | | | | | | |
|---|---|---|---|---|---|---|---|---|---|---|---|---|---|---|
| Gln | Arg | Lys | Arg | Asn | Thr | Ile | His | Glu | Phe | Lys | Lys | Ser | Ala | Lys |
| 1 | | | | 5 | | | | | 10 | | | | | 15 |
| Thr | Thr | Leu | Ile | Lys | Ile | Asp | Pro | Ala | Leu | Lys | Ile | Lys | Thr | Lys | Lys |
| | | | 20 | | | | | 25 | | | | | 30 | | |
| Val | Asn | Thr | Ala | Asp | Gln | Cys | Ala | Asn | Arg | Cys | Thr | Arg | Asn | Lys | Gly |
| | | | 35 | | | | | 40 | | | | | 45 | | |
| Leu | Pro | Phe | Thr | Cys | Lys | Ala | Phe | Val | Phe | Asp | Lys | Ala | Arg | Lys | Gln |
| | 50 | | | | | 55 | | | | | 60 | | | | |
| Cys | Leu | Trp | Phe | Pro | Phe | Asn | Ser | Met | Ser | Ser | Gly | Val | Lys | Lys | Glu |
| 65 | | | | | 70 | | | | | 75 | | | | | 80 |
| Phe | Gly | His | Glu | Phe | Asp | Leu | Tyr | Glu | Asn | Lys | Asp | Tyr | Ile | Arg | Asn |
| | | | | 85 | | | | | 90 | | | | | 95 | |
| Cys | Ile | Ile | Gly | Lys | Gly | Arg | Ser | Tyr | Lys | Gly | Thr | Val | Ser | Ile | Thr |
| | | | 100 | | | | | 105 | | | | | 110 | | |
| Lys | Ser | Gly | Ile | Lys | Cys | Gln | Pro | Trp | Ser | Ser | Met | Ile | Pro | His | Glu |
| | | | 115 | | | | | 120 | | | | | 125 | | |
| His | Arg | Phe | Leu | Pro | Ser | Ser | Tyr | Arg | Gly | Lys | Asp | Leu | Gln | Glu | Asn |
| | 130 | | | | | 135 | | | | | 140 | | | | |
| Tyr | Cys | Arg | Asn | Pro | Arg | Gly | Glu | Glu | Gly | Gly | Pro | Trp | Cys | Phe | Thr |
| 145 | | | | | 150 | | | | | 155 | | | | | 160 |
| Ser | Asn | Pro | Glu | Val | Arg | Tyr | Glu | Val | Cys | Asp | Ile | Pro | Gln | Cys | Ser |
| | | | | 165 | | | | | 170 | | | | | 175 | |
| Glu | Val | Glu | Cys | Met | Thr | Cys | Asn | Gly | Glu | Ser | Tyr | Arg | Gly | Leu | Met |
| | | | 180 | | | | | 185 | | | | | 190 | | |
| Asp | His | Thr | Glu | Ser | Gly | Lys | Ile | Cys | Gln | Arg | Trp | Asp | His | Gln | Thr |
| | | | 195 | | | | | 200 | | | | | 205 | | |
| Pro | His | Arg | His | Lys | Phe | Leu | Pro | Glu | Arg | Tyr | Pro | Asp | Lys | Gly | Phe |
| | 210 | | | | | 215 | | | | | 220 | | | | |
| Asp | Asp | Asn | Tyr | Cys | Arg | Asn | Pro | Asp | Gly | Gln | Pro | Arg | Pro | Trp | Cys |
| 225 | | | | | 230 | | | | | 235 | | | | | 240 |
| Tyr | Thr | Leu | Asp | Pro | His | Thr | Arg | Trp | Glu | Tyr | Cys | Ala | Ile | Lys | Thr |
| | | | | 245 | | | | | 250 | | | | | 255 | |
| Cys | Ala | Asp | Asn | Thr | Met | Asn | Asp | Thr | Asp | Val | Pro | Leu | Glu | Thr | Thr |
| | | | 260 | | | | | 265 | | | | | 270 | | |
| Glu | Cys | Ile | Gln | Gly | Gln | Gly | Glu | Gly | Tyr | Arg | Gly | Thr | Val | Asn | Thr |
| | | | 275 | | | | | 280 | | | | | 285 | | |
| Ile | Trp | Asn | Gly | Ile | Pro | Cys | Gln | Arg | Trp | Asp | Ser | Gln | Tyr | Pro | His |
| | 290 | | | | | 295 | | | | | 300 | | | | |
| Glu | His | Asp | Met | Thr | Pro | Glu | Asn | Phe | Lys | Cys | Lys | Asp | Leu | Arg | Glu |
| 305 | | | | | 310 | | | | | 315 | | | | | 320 |
| Asn | Tyr | Cys | Arg | Asn | Pro | Asp | Gly | Ser | Glu | Ser | Pro | Trp | Cys | Phe | Thr |
| | | | | 325 | | | | | 330 | | | | | 335 | |
| Thr | Asp | Pro | Asn | Ile | Arg | Val | Gly | Tyr | Cys | Ser | Gln | Ile | Pro | Asn | Cys |
| | | | 340 | | | | | 345 | | | | | 350 | | |
| Asp | Met | Ser | His | Gly | Gln | Asp | Cys | Tyr | Arg | Gly | Asn | Gly | Lys | Asn | Tyr |
| | | | 355 | | | | | 360 | | | | | 365 | | |
| Met | Gly | Asn | Leu | Ser | Gln | Thr | Arg | Ser | Gly | Leu | Thr | Cys | Ser | Met | Trp |
| | 370 | | | | | 375 | | | | | 380 | | | | |

```
Asp Lys Asn Met Glu Asp Leu His Arg His Ile Phe Trp Glu Pro Asp
385                 390                 395                 400

Ala Ser Lys Leu Asn Glu Asn Tyr Cys Arg Asn Pro Asp Asp Asp Ala
            405                 410                 415

His Gly Pro Trp Cys Tyr Thr Gly Asn Pro Leu Ile Pro Trp Asp Tyr
        420                 425                 430

Cys Pro Ile Ser Arg Cys Glu Gly Asp Thr Thr Pro Thr Ile Val Asn
    435                 440                 445

Leu Asp His Pro Val Ile Ser Cys Ala Lys Thr Lys Gln Leu Arg Val
450                 455                 460

Val Asn Gly Ile Pro Thr Arg Thr Asn Ile Gly Trp Met Val Ser Leu
465                 470                 475                 480

Arg Tyr Arg Asn Lys His Ile Cys Gly Gly Ser Leu Ile Lys Glu Ser
            485                 490                 495

Trp Val Leu Thr Ala Arg Gln Cys Phe Pro Ser Arg Asp Leu Lys Asp
        500                 505                 510

Tyr Glu Ala Trp Leu Gly Ile His Asp Val His Gly Arg Gly Asp Glu
    515                 520                 525

Lys Cys Lys Gln Val Leu Asn Val Ser Gln Leu Val Tyr Gly Pro Glu
530                 535                 540

Gly Ser Asp Leu Val Leu Met Lys Leu Ala Arg Pro Ala Val Leu Asp
545                 550                 555                 560

Asp Phe Val Ser Thr Ile Asp Leu Pro Asn Tyr Gly Cys Thr Ile Pro
            565                 570                 575

Glu Lys Thr Ser Cys Ser Val Tyr Gly Trp Gly Tyr Thr Gly Leu Ile
        580                 585                 590

Asn Tyr Asp Gly Leu Leu Arg Val Ala His Leu Tyr Ile Met Gly Asn
    595                 600                 605

Glu Lys Cys Ser Gln His His Arg Gly Lys Val Thr Leu Asn Glu Ser
610                 615                 620

Glu Ile Cys Ala Gly Ala Glu Lys Ile Gly Ser Gly Pro Cys Glu Gly
625                 630                 635                 640

Asp Tyr Gly Gly Pro Leu Val Cys Glu Gln His Lys Met Arg Met Val
            645                 650                 655

Leu Gly Val Ile Val Pro Gly Arg Gly Cys Ala Ile Pro Asn Arg Pro
        660                 665                 670

Gly Ile Phe Val Arg Val Ala Tyr Tyr Ala Lys Trp Ile His Lys Ile
    675                 680                 685

Ile Leu Thr Tyr Lys Val Pro Gln Ser
690                 695

<210> SEQ ID NO 3
<211> LENGTH: 697
<212> TYPE: PRT
<213> ORGANISM: artificial
<220> FEATURE:
<223> OTHER INFORMATION: amino acid sequence of 130His-hHGF

<400> SEQUENCE: 3

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45
```

```
Leu Pro Phe Thr Cys Lys Ala Phe Val Phe Asp Lys Ala Arg Lys Gln
    50              55                  60

Cys Leu Trp Phe Pro Phe Asn Ser Met Ser Ser Gly Val Lys Lys Glu
65              70              75                          80

Phe Gly His Glu Phe Asp Leu Tyr Glu Asn Lys Asp Tyr Ile Arg Asn
                85              90                  95

Cys Ile Ile Gly Lys Gly Arg Ser Tyr Lys Gly Thr Val Ser Ile Thr
                100             105             110

Lys Ser Gly Ile Lys Cys Gln Pro Trp Ser Ser Met Ile Pro His Glu
            115             120             125

His His Phe Leu Pro Ser Ser Tyr Arg Gly Lys Asp Leu Gln Glu Asn
    130             135             140

Tyr Cys Arg Asn Pro Arg Gly Glu Glu Gly Gly Pro Trp Cys Phe Thr
145             150             155                         160

Ser Asn Pro Glu Val Arg Tyr Glu Val Cys Asp Ile Pro Gln Cys Ser
                165             170             175

Glu Val Glu Cys Met Thr Cys Asn Gly Glu Ser Tyr Arg Gly Leu Met
            180             185             190

Asp His Thr Glu Ser Gly Lys Ile Cys Gln Arg Trp Asp His Gln Thr
    195             200             205

Pro His Arg His Lys Phe Leu Pro Glu Arg Tyr Pro Asp Lys Gly Phe
    210             215             220

Asp Asp Asn Tyr Cys Arg Asn Pro Asp Gly Gln Pro Arg Pro Trp Cys
225             230             235                         240

Tyr Thr Leu Asp Pro His Thr Arg Trp Glu Tyr Cys Ala Ile Lys Thr
                245             250             255

Cys Ala Asp Asn Thr Met Asn Asp Thr Asp Val Pro Leu Glu Thr Thr
            260             265             270

Glu Cys Ile Gln Gly Gln Gly Glu Gly Tyr Arg Gly Thr Val Asn Thr
    275             280             285

Ile Trp Asn Gly Ile Pro Cys Gln Arg Trp Asp Ser Gln Tyr Pro His
    290             295             300

Glu His Asp Met Thr Pro Glu Asn Phe Lys Cys Lys Asp Leu Arg Glu
305             310             315                         320

Asn Tyr Cys Arg Asn Pro Asp Gly Ser Glu Ser Pro Trp Cys Phe Thr
                325             330             335

Thr Asp Pro Asn Ile Arg Val Gly Tyr Cys Ser Gln Ile Pro Asn Cys
            340             345             350

Asp Met Ser His Gly Gln Asp Cys Tyr Arg Gly Asn Gly Lys Asn Tyr
            355             360             365

Met Gly Asn Leu Ser Gln Thr Arg Ser Gly Leu Thr Cys Ser Met Trp
    370             375             380

Asp Lys Asn Met Glu Asp Leu His Arg His Ile Phe Trp Glu Pro Asp
385             390             395                         400

Ala Ser Lys Leu Asn Glu Asn Tyr Cys Arg Asn Pro Asp Asp Asp Ala
                405             410             415

His Gly Pro Trp Cys Tyr Thr Gly Asn Pro Leu Ile Pro Trp Asp Tyr
            420             425             430

Cys Pro Ile Ser Arg Cys Glu Gly Asp Thr Thr Pro Thr Ile Val Asn
            435             440             445

Leu Asp His Pro Val Ile Ser Cys Ala Lys Thr Lys Gln Leu Arg Val
    450             455             460

Val Asn Gly Ile Pro Thr Arg Thr Asn Ile Gly Trp Met Val Ser Leu
```

-continued

```
            465                 470                 475                 480
        Arg Tyr Arg Asn Lys His Ile Cys Gly Gly Ser Leu Ile Lys Glu Ser
                        485                 490                 495

Trp Val Leu Thr Ala Arg Gln Cys Phe Pro Ser Arg Asp Leu Lys Asp
                        500                 505                 510

Tyr Glu Ala Trp Leu Gly Ile His Asp Val His Gly Arg Gly Asp Glu
                        515                 520                 525

Lys Cys Lys Gln Val Leu Asn Val Ser Gln Leu Val Tyr Gly Pro Glu
                        530                 535                 540

Gly Ser Asp Leu Val Leu Met Lys Leu Ala Arg Pro Ala Val Leu Asp
        545                 550                 555                 560

Asp Phe Val Ser Thr Ile Asp Leu Pro Asn Tyr Gly Cys Thr Ile Pro
                        565                 570                 575

Glu Lys Thr Ser Cys Ser Val Tyr Gly Trp Gly Tyr Thr Gly Leu Ile
                        580                 585                 590

Asn Tyr Asp Gly Leu Leu Arg Val Ala His Leu Tyr Ile Met Gly Asn
                        595                 600                 605

Glu Lys Cys Ser Gln His His Arg Gly Lys Val Thr Leu Asn Glu Ser
                        610                 615                 620

Glu Ile Cys Ala Gly Ala Glu Lys Ile Gly Ser Gly Pro Cys Glu Gly
        625                 630                 635                 640

Asp Tyr Gly Gly Pro Leu Val Cys Glu Gln His Lys Met Arg Met Val
                        645                 650                 655

Leu Gly Val Ile Val Pro Gly Arg Gly Cys Ala Ile Pro Asn Arg Pro
                        660                 665                 670

Gly Ile Phe Val Arg Val Ala Tyr Tyr Ala Lys Trp Ile His Lys Ile
                        675                 680                 685

Ile Leu Thr Tyr Lys Val Pro Gln Ser
                        690                 695

<210> SEQ ID NO 4
<211> LENGTH: 697
<212> TYPE: PRT
<213> ORGANISM: artificial
<220> FEATURE:
<223> OTHER INFORMATION: amino acid sequence of 130Lys-hHGF

<400> SEQUENCE: 4

Gln Arg Lys Arg Arg Asn Thr Ile His Glu Phe Lys Lys Ser Ala Lys
        1               5                   10                  15

Thr Thr Leu Ile Lys Ile Asp Pro Ala Leu Lys Ile Lys Thr Lys Lys
                        20                  25                  30

Val Asn Thr Ala Asp Gln Cys Ala Asn Arg Cys Thr Arg Asn Lys Gly
                        35                  40                  45

Leu Pro Phe Thr Cys Lys Ala Phe Val Phe Asp Lys Ala Arg Lys Gln
                        50                  55                  60

Cys Leu Trp Phe Pro Phe Asn Ser Met Ser Ser Gly Val Lys Lys Glu
        65                  70                  75                  80

Phe Gly His Glu Phe Asp Leu Tyr Glu Asn Lys Asp Tyr Ile Arg Asn
                        85                  90                  95

Cys Ile Ile Gly Lys Gly Arg Ser Tyr Lys Gly Thr Val Ser Ile Thr
                        100                 105                 110

Lys Ser Gly Ile Lys Cys Gln Pro Trp Ser Ser Met Ile Pro His Glu
                        115                 120                 125

His Lys Phe Leu Pro Ser Ser Tyr Arg Gly Lys Asp Leu Gln Glu Asn
```

-continued

```
            130                 135                 140
Tyr Cys Arg Asn Pro Arg Gly Glu Glu Gly Pro Trp Cys Phe Thr
145                 150                 155                 160

Ser Asn Pro Glu Val Arg Tyr Glu Val Cys Asp Ile Pro Gln Cys Ser
                    165                 170                 175

Glu Val Glu Cys Met Thr Cys Asn Gly Glu Ser Tyr Arg Gly Leu Met
                180                 185                 190

Asp His Thr Glu Ser Gly Lys Ile Cys Gln Arg Trp Asp His Gln Thr
                195                 200                 205

Pro His Arg His Lys Phe Leu Pro Glu Arg Tyr Pro Asp Lys Gly Phe
210                 215                 220

Asp Asp Asn Tyr Cys Arg Asn Pro Asp Gly Gln Pro Arg Pro Trp Cys
225                 230                 235                 240

Tyr Thr Leu Asp Pro His Thr Arg Trp Glu Tyr Cys Ala Ile Lys Thr
                245                 250                 255

Cys Ala Asp Asn Thr Met Asn Asp Thr Asp Val Pro Leu Glu Thr Thr
                260                 265                 270

Glu Cys Ile Gln Gly Gln Gly Glu Gly Tyr Arg Gly Thr Val Asn Thr
                275                 280                 285

Ile Trp Asn Gly Ile Pro Cys Gln Arg Trp Asp Ser Gln Tyr Pro His
290                 295                 300

Glu His Asp Met Thr Pro Glu Asn Phe Lys Cys Lys Asp Leu Arg Glu
305                 310                 315                 320

Asn Tyr Cys Arg Asn Pro Asp Gly Ser Glu Ser Pro Trp Cys Phe Thr
                325                 330                 335

Thr Asp Pro Asn Ile Arg Val Gly Tyr Cys Ser Gln Ile Pro Asn Cys
                340                 345                 350

Asp Met Ser His Gly Gln Asp Cys Tyr Arg Gly Asn Gly Lys Asn Tyr
                355                 360                 365

Met Gly Asn Leu Ser Gln Thr Arg Ser Gly Leu Thr Cys Ser Met Trp
                370                 375                 380

Asp Lys Asn Met Glu Asp Leu His Arg His Ile Phe Trp Glu Pro Asp
385                 390                 395                 400

Ala Ser Lys Leu Asn Glu Asn Tyr Cys Arg Asn Pro Asp Asp Asp Ala
                405                 410                 415

His Gly Pro Trp Cys Tyr Thr Gly Asn Pro Leu Ile Pro Trp Asp Tyr
                420                 425                 430

Cys Pro Ile Ser Arg Cys Glu Gly Asp Thr Thr Pro Thr Ile Val Asn
                435                 440                 445

Leu Asp His Pro Val Ile Ser Cys Ala Lys Thr Lys Gln Leu Arg Val
450                 455                 460

Val Asn Gly Ile Pro Thr Arg Thr Asn Ile Gly Trp Met Val Ser Leu
465                 470                 475                 480

Arg Tyr Arg Asn Lys His Ile Cys Gly Gly Ser Leu Ile Lys Glu Ser
                485                 490                 495

Trp Val Leu Thr Ala Arg Gln Cys Phe Pro Ser Arg Asp Leu Lys Asp
                500                 505                 510

Tyr Glu Ala Trp Leu Gly Ile His Asp Val His Gly Arg Gly Asp Glu
                515                 520                 525

Lys Cys Lys Gln Val Leu Asn Val Ser Gln Leu Val Tyr Gly Pro Glu
530                 535                 540

Gly Ser Asp Leu Val Leu Met Lys Leu Ala Arg Pro Ala Val Leu Asp
545                 550                 555                 560
```

```
Asp Phe Val Ser Thr Ile Asp Leu Pro Asn Tyr Gly Cys Thr Ile Pro
            565                 570                 575
Glu Lys Thr Ser Cys Ser Val Tyr Gly Trp Gly Tyr Thr Gly Leu Ile
        580                 585                 590
Asn Tyr Asp Gly Leu Leu Arg Val Ala His Leu Tyr Ile Met Gly Asn
    595                 600                 605
Glu Lys Cys Ser Gln His His Arg Gly Lys Val Thr Leu Asn Glu Ser
610                 615                 620
Glu Ile Cys Ala Gly Ala Glu Lys Ile Gly Ser Gly Pro Cys Glu Gly
625                 630                 635                 640
Asp Tyr Gly Gly Pro Leu Val Cys Glu Gln His Lys Met Arg Met Val
                645                 650                 655
Leu Gly Val Ile Val Pro Gly Arg Gly Cys Ala Ile Pro Asn Arg Pro
            660                 665                 670
Gly Ile Phe Val Arg Val Ala Tyr Tyr Ala Lys Trp Ile His Lys Ile
        675                 680                 685
Ile Leu Thr Tyr Lys Val Pro Gln Ser
    690                 695
```

<210> SEQ ID NO 5
<211> LENGTH: 2094
<212> TYPE: DNA
<213> ORGANISM: Homo sapiens

<400> SEQUENCE: 5

```
caaaggaaaa gaagaaatac aattcatgaa ttcaaaaaat cagcaaagac taccctaatc    60
aaaatagatc cagcactgaa gataaaaacc aaaaaagtga atactgcaga ccaatgtgct   120
aatagatgta ctaggaataa aggcttcca ttcacttgca aggcttttgt ttttgataaa    180
gcaagaaaac aatgcctctg gttccccttc aatagcatgt caagtggagt gaaaaaagaa   240
tttggccatg aatttgacct ctatgaaaac aaagactaca ttagaaactg catcattggt   300
aaaggacgca gctacaaggg aacagtatct atcactaaga gtggcatcaa atgtcagccc   360
tggagttcca tgataccaca cgaacacagc tttttgcctt cgagctatcg ggtaaaagac   420
ctacaggaaa actactgtcg aaatcctcga ggggaagaag ggggaccctg tgtttcaca    480
agcaatccag aggtacgcta cgaagtctgt gacattcctc agtgttcaga gttgaatgc    540
atgacctgca atggggagag ttatcgaggt ctcatggatc atacagaatc aggcaagatt   600
tgtcagcgct gggatcatca gacaccacac cggcacaaat tcttgcctga agatatcccc   660
gacaagggct tgatgataaa ttattgccgc aatccgatg gccagccgag gccatggtgc   720
tatactcttg accctcacac ccgctgggag tactgtgcaa ttaaaacatg cgctgacaat   780
actatgaatg acactgatgt tcctttggaa caactgaat gcatccaagg tcaaggagaa   840
ggctacaggg gcactgtcaa taccatttgg aatggaattc catgtcagcg ttgggattct   900
cagtatcctc acgagcatga catgactcct gaaaatttca gtgcaagga cctacgagaa   960
aattactgcc gaaatccaga tgggtctgaa tcaccctggt gttttaccac tgatccaaac  1020
atccgagttg gctactgctc ccaaattcca actgtgata tgtcacatgg acaagattgt  1080
tatcgtggga atggcaaaaa ttatatgggc aacttatccc aaacaagatc tggactaaca  1140
tgttcaatgt gggacaagaa catggaagac ttcatcgtc atatcttctg ggaaccagat  1200
gcaagtaagc tgaatgagaa ttactgccga aatccagatg atgatgctca tggacccgg  1260
tgctacacgg gaaatccact cattccttgg gattattgcc ctatttctcg ttgtgaaggt  1320
```

```
gataccacac ctacaatagt caatttagac catcccgtaa tatcttgtgc caaaacgaaa      1380
caattgcgag ttgtaaatgg gattccaaca cgaacaaaca taggatggat ggttagtttg      1440
agatacagaa ataaacatat ctgcggagga tcattgataa aggagagttg ggttcttact      1500
gcacgacagt gtttcccttc tcgagacttg aaagattatg aagcttggct tggaattcat      1560
gatgtccacg gaagaggaga tgagaaatgc aaacaggttc tcaatgtttc ccagctggta      1620
tatgcccctg aaggatcaga tctggtttta atgaagcttg ccaggcctgc tgtcctggat      1680
gattttgtta gtacgattga tttacctaat tatggatgca caattcctga aaagaccagt      1740
tgcagtgttt atggctgggg ctacactgga ttgatcaact atgatggcct attacgagtg      1800
gcacatctct atataatggg aaatgagaaa tgcagccagc atcatcgagg aaggtgact      1860 ctgaatgagt ctgaaatatg tgctggggct gaaaagattg gatcaggacc atgtgagggg      1920
gattatggtg gcccacttgt ttgtgagcaa cataaaatga gaatggttct tggtgtcatt      1980
gttcctggtc gtggatgtgc cattccaaat cgtcctggta tttttgtccg agtagcatat      2040
tatgcaaaat ggatacacaa aattattta acatataagg taccacagtc atag            2094

<210> SEQ ID NO 6
<211> LENGTH: 2094
<212> TYPE: DNA
<213> ORGANISM: artificial
<220> FEATURE:
<223> OTHER INFORMATION: nucleotide sequence encoding 130Arg-hHGF

<400> SEQUENCE: 6
caaaggaaaa gaagaaatac aattcatgaa ttcaaaaaat cagcaaagac taccctaatc       60
aaaatagatc cagcactgaa gataaaaacc aaaaaagtga atactgcaga ccaatgtgct      120
aatagatgta ctaggaataa aggacttcca ttcacttgca aggcttttgt ttttgataaa      180
gcaagaaaac aatgcctctg gttccccttc aatagcatgt caagtggagt gaaaaaagaa      240
tttggccatg aatttgacct ctatgaaaac aaagactaca ttagaaactg catcattggt      300
aaaggacgca gctacaaggg aacagtatct atcactaaga gtggcatcaa atgtcagccc      360
tggagttcca tgataccaca cgaacacaga tttttgcctt cgagctatcg ggtaaagac       420 ctacaggaaa actactgtcg aaatcctcga ggggaagaag ggggaccctg tgtttcaca       480 agcaatccag aggtacgcta cgaagtctgt gacattcctc agtgttcaga agttgaatgc      540
atgacctgca tggggagag ttatcgaggt ctcatggatc atacagaatc aggcaagatt      600
tgtcagcgct gggatcatca gacaccacac cggcacaaat tcttgcctga agatatccc       660 gacaagggct tgatgataa ttattgccgc aatcccgatg ccagccgag gccatggtgc      720 tatactcttg accctcacac ccgctgggag tactgtgcaa ttaaaacatg cgctgacaat      780
actatgaatg acactgatgt tccctttgga acaactgaat gcatccaagg tcaaggagaa      840
ggctacaggg gcactgtcaa taccatttgg aatggaattc catgtcagcg ttgggattct      900
cagtatcctc acgagcatga catgactcct gaaaatttca gtgcaagga cctacgagaa      960 aattactgcc gaaatccaga tgggtctgaa tcaccctggt gttttaccac tgatccaaac     1020
atccgagttg gctactgctc ccaaattcca aactgtgata tgtcacatgg acaagattgt     1080
tatcgtggga atggcaaaaa ttatatgggc aacttatccc aaacaagatc tggactaaca     1140
tgttcaatgt gggacaagaa catggaagac ttacatcgtc atatcttctg gaaccagat      1200 gcaagtaagc tgaatgagaa ttactgccga atccagtgatg atgatgctca tggaccctgg     1260
```

```
tgctacacgg gaaatccact cattccttgg gattattgcc ctatttctcg ttgtgaaggt   1320
gataccacac ctacaatagt caatttagac catcccgtaa tatcttgtgc caaaacgaaa   1380
caattgcgag ttgtaaatgg gattccaaca cgaacaaaca taggatggat ggttagtttg   1440
agatacagaa ataaacatat ctgcggagga tcattgataa aggagagttg ggttcttact   1500
gcacgacagt gtttcccttc tcgagacttg aaagattatg aagcttggct tggaattcat   1560
gatgtccacg gaagaggaga tgagaaatgc aaacaggttc tcaatgtttc ccagctggta   1620
tatgcccctg aaggatcaga tctggtttta atgaagcttg ccaggcctgc tgtcctggat   1680
gattttgtta gtacgattga tttacctaat tatggatgca caattcctga aaagaccagt   1740
tgcagtgttt atggctgggg ctacactgga ttgatcaact atgatggcct attacgagtg   1800
gcacatctct atataatggg aaatgagaaa tgcagccagc atcatcgagg aaggtgact   1860 ctgaatgagt ctgaaatatg tgctggggct gaaaagattg gatcaggacc atgtgagggg   1920
gattatggtg gcccacttgt ttgtgagcaa cataaaatga gaatggttct tggtgtcatt   1980
gttcctggtc gtgatgtgc cattccaaat cgtcctggta tttttgtccg agtagcatat   2040
tatgcaaaat ggatacacaa aattattta acatataagg taccacagtc atag          2094

<210> SEQ ID NO 7
<211> LENGTH: 2094
<212> TYPE: DNA
<213> ORGANISM: artificial
<220> FEATURE:
<223> OTHER INFORMATION: nucleotide sequence encoding 130His-hHGF

<400> SEQUENCE: 7
caaaggaaaa gaagaaatac aattcatgaa ttcaaaaaat cagcaaagac taccctaatc     60
aaaatagatc cagcactgaa gataaaaacc aaaaaagtga atactgcaga ccaatgtgct    120
aatagatgta ctaggaataa aggacttcca ttcacttgca aggcttttgt ttttgataaa    180
gcaagaaaac aatgcctctg gttccccttc aatagcatgt caagtggagt gaaaaaagaa    240
tttggccatg aatttgacct ctatgaaaac aaagactaca ttagaaactg catcattggt    300
aaaggacgca gctacaaggg aacagtatct atcactaaga gtggcatcaa atgtcagccc    360
tggagttcca tgataccaca cgaacaccac tttttgcctt cgagctatcg gggtaaagac    420
ctacaggaaa actactgtcg aaatcctcga ggggaagaag ggggaccctg tgttttcaca    480
agcaatccag aggtacgcta cgaagtctgt gacattcctc agtgttcaga agttgaatgc    540
atgacctgca atggggagag ttatcgaggt ctcatggatc atacagaatc aggcaagatt    600
tgtcagcgct gggatcatca gacaccacac cggcacaaat tcttgcctga agatatccc    660 gacaagggct tgatgataa ttattgccgc aatcccgatg ccagccgag gcatggtgc     720 tatactcttg accctcacac ccgctgggag tactgtgcaa ttaaaacatg cgctgacaat   780
actatgaatg acactgatgt tccttttgaa caaactgaat gcatccaagg tcaaggagaa   840
ggctacaggg gcactgtcaa taccatttgg aatggaattc catgtcagcg ttgggattct   900
cagtatcctc acgagcatga catgactcct gaaaatttca gtgcaagga cctacgagaa   960 aattactgcc gaaatccaga tgggtctgaa tcacccgtgt gttaccac tgatccaaac  1020 atccgagttg gctactgctc ccaaattcca aactgtgata tgtcacatgg acaagattgt  1080
tatcgtggga atgcaaaaaa ttatatgggc aacttatccc aaacaagatc tggactaaca  1140
tgttcaatgt gggacaagaa catggaagac ttacatcgtc atatcttctg ggaaccagat  1200
gcaagtaagc tgaatgagaa ttactgccga aatccagatg atgatgctca tggaccctgg  1260
```

```
tgctacacgg gaaatccact cattccttgg gattattgcc ctatttctcg ttgtgaaggt    1320
gataccacac ctacaatagt caatttagac catcccgtaa tatcttgtgc caaaacgaaa    1380
caattgcgag ttgtaaatgg gattccaaca cgaacaaaca taggatggat ggttagtttg    1440
agatacagaa ataaacatat ctgcggagga tcattgataa aggagagttg ggttcttact    1500
gcacgacagt gtttcccttc tcgagacttg aaagattatg aagcttggct tggaattcat    1560
gatgtccacg gaagaggaga tgagaaatgc aaacaggttc tcaatgtttc ccagctggta    1620
tatggccctg aaggatcaga tctggtttta atgaagcttg ccaggcctgc tgtcctggat    1680
gattttgtta gtacgattga tttacctaat tatggatgca caattcctga aaagaccagt    1740
tgcagtgttt atggctgggg ctacactgga ttgatcaact atgatggcct attacgagtg    1800
gcacatctct atataatggg aaatgagaaa tgcagccagc atcatcgagg aaggtgact    1860 ctgaatgagt ctgaaatatg tgctggggct gaaaagattg gatcaggacc atgtgagggg    1920
gattatggtg gcccacttgt ttgtgagcaa cataaaatga aatggttct tggtgtcatt    1980 gttcctggtc gtggatgtgc cattccaaat cgtcctggta ttttttgtccg agtagcatat    2040 tatgcaaaat ggatacacaa aattattta acatataagg taccacagtc atag           2094

<210> SEQ ID NO 8
<211> LENGTH: 2094
<212> TYPE: DNA
<213> ORGANISM: artificial
<220> FEATURE:
<223> OTHER INFORMATION: nucleotide sequence encoding 130Lys-hHGF

<400> SEQUENCE: 8
caaaggaaaa gaagaaatac aattcatgaa ttcaaaaaat cagcaaagac taccctaatc      60
aaaatagatc cagcactgaa gataaaaacc aaaaaagtga atactgcaga ccaatgtgct     120
aatagatgta ctaggaataa aggacttcca ttcacttgca aggcttttgt ttttgataaa     180
gcaagaaaac aatgcctctg gttccccttc aatagcatgt caagtggagt gaaaaaagaa     240
tttggccatg aatttgacct ctatgaaaac aaagactaca ttagaaactg catcattggt     300
aaaggacgca gctacaaggg aacagtatct atcactaaga gtggcatcaa atgtcagccc     360
tggagttcca tgataccaca cgaacacaag ttttttgcctt cgagctatcg gggtaaagac     420
ctacaggaaa actactgtcg aaatcctcga ggggaagaag ggggaccctg tgtttcaca      480 agcaatccag aggtacgcta cgaagtctgt gacattcctc agtgttcaga agttgaatgc      540
atgacctgca tggggagag ttatcgaggt ctcatggatc atacagaatc aggcaagatt      600
tgtcagcgct gggatcatca gacaccacac cggcacaaat tcttgcctga agatatccc      660 gacaagggct tgatgataa ttattgccgc aatcccgatg ccagccgag ccatggtgc       720 tatactcttg acctcacac ccgctgggag tactgtgcaa ttaaaacatg cgctgacaat      780
actatgaatg acactgatgt tcctttggaa caactgaatg catccaagg tcaaggagaa      840 ggctacaggg gcactgtcaa taccatttgg aatggaattc catgtcagcg ttgggattct      900
cagtatcctc acgagcatga catgactcct gaaaatttca gtgcaagga cctacgagaa      960 aattactgcc gaaatccaga tgggtctgaa tcaccctggt gttttaccac tgatccaaac    1020
atccgagttg gctactgctc ccaaattcca aactgtgata tgtcacatgg acaagattgt    1080
tatcgtggga tggcaaaaa ttatgtggc aacttatccc aaacaagatc tggactaaca   1140
tgttcaatgt gggacaagaa catggaagac ttacatcgtc atatcttctg ggaaccagat    1200
```

| | |
|---|---|
| gcaagtaagc tgaatgagaa ttactgccga aatccagatg atgatgctca tggaccctgg | 1260 |
| tgctacacgg gaaatccact cattccttgg gattattgcc ctatttctcg ttgtgaaggt | 1320 |
| gataccacac ctacaatagt caatttagac catcccgtaa tatcttgtgc caaaacgaaa | 1380 |
| caattgcgag ttgtaaatgg gattccaaca cgaacaaaca taggatggat ggttagtttg | 1440 |
| agatacagaa ataaacatat ctgcggagga tcattgataa aggagagttg ggttcttact | 1500 |
| gcacgacagt gtttcccttc tcgagacttg aaagattatg aagcttggct tggaattcat | 1560 |
| gatgtccacg gaagaggaga tgagaaatgc aaacaggttc tcaatgtttc ccagctggta | 1620 |
| tatggccctg aaggatcaga tctggttttta atgaagcttg ccaggcctgc tgtcctggat | 1680 |
| gattttgtta gtacgattga tttacctaat tatggatgca caattcctga aaagaccagt | 1740 |
| tgcagtgttt atggctgggg ctacactgga ttgatcaact atgatggcct attacgagtg | 1800 |
| gcacatctct atataatggg aaatgagaaa tgcagccagc atcatcgagg aaggtgact | 1860 |
| ctgaatgagt ctgaaatatg tgctggggct gaaaagattg gatcaggacc atgtgagggg | 1920 |
| gattatggtg gcccacttgt ttgtgagcaa cataaaatga gaatggttct tggtgtcatt | 1980 |
| gttcctggtc gtggatgtgc cattccaaat cgtcctggta tttttgtccg agtagcatat | 2040 |
| tatgcaaaat ggatacacaa aattatttta acatataagg taccacagtc atag | 2094 |

```
<210> SEQ ID NO 9
<211> LENGTH: 2889
<212> TYPE: DNA
<213> ORGANISM: artificial
<220> FEATURE:
<223> OTHER INFORMATION: nucleotide sequence of pSN vector

<400> SEQUENCE: 9
```

| | |
|---|---|
| gcgcagcacc atggcctgaa ataacctctg aaagaggaac ttggttaggt accttctgag | 60 |
| gcggaaagaa ccagctgtgg aatgtgtgtc agttagggtg tggaaagtcc ccaggctccc | 120 |
| cagcaggcag aagtatgcaa agcatgcatc tcaattagtc agcaaccagg tgtggaaagt | 180 |
| ccccaggctc cccagcaggc agaagtatgc aaagcatgca tctcaattag tcagcaacca | 240 |
| tagtcccgcc cctaactccg cccatcccgc cctaactccc gcccagttcc gcccattctc | 300 |
| cgccccatgg ctgactaatt tttttttattt atgcagaggc cgaggccgcc tcggcctctg | 360 |
| agctattcca gaagtagtga ggaggctttt tggaggcct aggcttttgc aaaaagcttg | 420 |
| ctagccaccg cggccgcaac ttgtttattg cagcttataa tggttacaaa taaagcaata | 480 |
| gcatcacaaa tttcacaaat aaagcatttt tttcactgca ttctagttgt ggtttgtcca | 540 |
| aactcatcaa tgtatcttat catgtctgga tccaggataa tatatggtag ggttcatagc | 600 |
| cagagtaacc tttttttttta attttttattt tattttattt tgagctgcag gcatgcaagc | 660 |
| tggcactggc cgtcgtttta caacgtcgtg actgggaaaa ccctggcgtt acccaactta | 720 |
| atcgccttgc agcacatccc cctttcgcca gctggcgtaa tagcgaagag gcccgcaccg | 780 |
| atcgccttc ccaacagttg cgcagcctga atggcgaatg gcgcctgatg cggtattttc | 840 |
| tccttacgca tctgtgcggt atttcacacc gcatatggtg cactctcagt acaatctgct | 900 |
| ctgatgccgc atagttaagc cagccccgac acccgccaac acccgctgac gcgccctgac | 960 |
| gggcttgtct gctcccggca tccgcttaca gacaagctgt gaccgtctcc gggagctgca | 1020 |
| tgtgtcagag gttttcaccg tcatcaccga aacgcgcgag acgaaagggc ctcgtgatac | 1080 |
| gcctattttt ataggttaat gtcatgataa taatggtttc ttagacgtca ggtggcactt | 1140 |
| ttcggggaaa tgtgcgcgga accctatttg tttatttttt ctaaatacat tcaaatatgt | 1200 |

-continued

```
atccgctcat gagacaataa ccctgataaa tgcttcaata atattgaaaa aggaagagta    1260
tgctggggag tcgaaattca gaagaactcg tcaagaaggc gatagaaggc gatgcgctgc    1320
gaatcgggag cggcgatacc gtaaagcacg aggaagcggt cagcccattc gccgccaagc    1380
tcttcagcaa tatcacgggt agccaacgct atgtcctgat agcggtccgc cacacccagc    1440
cggccacagt cgatgaatcc agaaaagcgg ccattttcca ccatgatatt cggcaagcag    1500
gcatcgccat gggtcacgac gagatcctcg ccgtcgggca tgctcgcctt gagcctggcg    1560
aacagttcgg ctggcgcgag cccctgatgc tcttcgtcca gatcatcctg atcgacaaga    1620
ccggcttcca tccgagtacg tgctcgctcg atgcgatgtt tcgcttggtg gtcgaatggg    1680
caggtagccg gatcaagcgt atgcagccgc cgcattgcat cagccatgat ggatactttc    1740
tcggcaggag caaggtgaga tgacaggaga tcctgccccg gcacttcgcc caatagcagc    1800
cagtcccttc ccgcttcagt gacaacgtcg agcacagctg cgcaaggaac gcccgtcgtg    1860
gccagccacg atagccgcgc tgcctcgtct tgcagttcat tcagggcacc ggacaggtcg    1920
gtcttgacaa aaagaaccgg gcgcccctgc gctgacagcc ggaacacggc ggcatcagag    1980
cagccgattg tctgttgtgc ccagtcatag ccgaatagcc tctccaccca agcggccgga    2040
gaacctgcgt gcaatccatc ttgttcaatc atgcgaaacg atcctcatcc tgtctcttga    2100
tcagatcttg atccctgtca gaccaagttt actcatatat actttagatt gatttaaaac    2160 ttcatttta atttaaaagg atctaggtga agatccttt tgataatctc atgaccaaaa      2220
tcccttaacg tgagttttcg ttccactgag cgtcagaccc cgtagaaaag atcaaaggat    2280
cttcttgaga tcctttttt ctgcgcgtaa tctgctgctt gcaaacaaaa aaaccaccgc     2340
taccagcggt ggtttgtttg ccggatcaag agctaccaac tctttttccg aaggtaactg    2400
gcttcagcag agcgcagata ccaaatactg ttcttctagt gtagccgtag ttaggccacc    2460
acttcaagaa ctctgtagca ccgcctacat acctcgctct gctaatcctg ttaccagtgg    2520
ctgctgccag tggcgataag tcgtgtctta ccgggttgga ctcaagacga tagttaccgg    2580
ataaggcgca gcggtcgggc tgaacggggg gttcgtgcac acagcccagc ttggagcgaa    2640
cgacctacac cgaactgaga tacctacagc gtgagctatg agaaagcgcc acgcttcccg    2700
aagggagaaa ggcggacagg tatccggtaa gcggcagggt cggaacagga gagcgcacga    2760
gggagcttcc aggggaaac gcctggtatc tttatagtcc tgtcgggttt cgccacctct     2820
gacttgagcg tcgatttttg tgatgctcgt caggggggcg gagcctatgg aaaaacgcca    2880
gcaacgcgg                                                            2889
```